United States Patent
Adamo et al.

(10) Patent No.: US 9,016,147 B2
(45) Date of Patent: Apr. 28, 2015

(54) APPARATUS AND METHOD FOR SIMULATING INHALATION EFFORTS

(75) Inventors: Benoit Adamo, Mount Kisko, NY (US); John M. Polidoro, Coventry, CT (US); Dennis Overfield, Fairfield, CT (US); Carl R. Sahi, Coventry, CT (US); Brendan Laurenzi, New Milford, CT (US); Chad C. Smutney, Watertown, CT (US); Spencer P. Kinsey, Sandy Hook, CT (US)

(73) Assignee: MannKind Corporation, Valencia, CA (US)

(*) Notice: Subject to any disclaimer, the term of this patent is extended or adjusted under 35 U.S.C. 154(b) by 356 days.

(21) Appl. No.: 13/505,729

(22) PCT Filed: Nov. 3, 2010

(86) PCT No.: PCT/US2010/055323
§ 371 (c)(1),
(2), (4) Date: Jun. 19, 2012

(87) PCT Pub. No.: WO2011/056889
PCT Pub. Date: May 12, 2011

(65) Prior Publication Data
US 2012/0247235 A1    Oct. 4, 2012

Related U.S. Application Data

(60) Provisional application No. 61/257,813, filed on Nov. 3, 2009.

(51) Int. Cl.
*A61B 5/00*    (2006.01)
*A61B 5/08*    (2006.01)
(Continued)

(52) U.S. Cl.
CPC .............. *A61B 5/08* (2013.01); *A61B 5/4839* (2013.01); *A61B 7/003* (2013.01);
(Continued)

(58) Field of Classification Search
USPC .............................. 73/865.4, 865.9
See application file for complete search history.

(56) References Cited

U.S. PATENT DOCUMENTS

| 4,811,731 A | 3/1989 | Newell et al. |
| 6,279,511 B1 | 8/2001 | Loughnane |

(Continued)

FOREIGN PATENT DOCUMENTS

| JP | 2007-061281 | 3/2007 |
| WO | 2002/059574 A1 | 8/2002 |

(Continued)

OTHER PUBLICATIONS

Boer et al., Design and application of a new modular adapter for laser diffraction characterization of inhalation aerosols. International Jornal of Pharmaceutics 249, pp. 233-245 (2002).

(Continued)

*Primary Examiner* — Peter Macchiarolo
*Assistant Examiner* — Nathaniel Kolb
(74) *Attorney, Agent, or Firm* — K&L Gates LLP; Louis C. Cullman; Robert W. Winn

(57) ABSTRACT

An inhalation simulation system is provided for use with inhalers in particular breath-powered dry powder inhalers. The simulation system can recreate a patient's inhalation profile obtained with an inhaler adapted with a sensing and monitoring device for the detection of characteristic signals generated from the inhaler in use, which signals are transmitted to a computer with an algorithm which is configured to analyze the signals and generate new signals via a transmitter to actuate the inhalation simulation system component parts so that a subject's inhalation profile is replicated simultaneously or in real-time, or stored for later use. Methods of measuring the performance of inhalers are also provided.

20 Claims, 20 Drawing Sheets

(51) Int. Cl.

| | | |
|---|---|---|
| *A61K 9/00* | (2006.01) | |
| *A61K 31/496* | (2006.01) | |
| *A61M 15/00* | (2006.01) | |
| *G09B 19/00* | (2006.01) | |
| *G09B 23/28* | (2006.01) | |
| *A61M 16/16* | (2006.01) | |
| *A61B 7/00* | (2006.01) | |
| *A61M 16/00* | (2006.01) | |

(52) U.S. Cl.
CPC .............. *A61K 9/0075* (2013.01); *A61K 31/496* (2013.01); *A61M 15/0028* (2013.01); *A61M 2016/0021* (2013.01); *A61M 2016/0027* (2013.01); *A61M 2016/003* (2013.01); *A61M 2202/064* (2013.01); *A61M 2205/3368* (2013.01); *A61M 2205/3375* (2013.01); *A61M 2205/3569* (2013.01); *A61M 2205/3592* (2013.01); *A61M 2205/50* (2013.01); *A61M 2205/502* (2013.01); *A61M 2205/8206* (2013.01); *G09B 19/003* (2013.01); *G09B 23/28* (2013.01); *A61M 16/161* (2013.01)

(56) References Cited

U.S. PATENT DOCUMENTS

| | | |
|---|---|---|
| 7,305,986 B1 | 12/2007 | Steiner et al. |
| 7,414,720 B2 | 8/2008 | Wachtel et al. |
| 7,453,556 B2 | 11/2008 | Hochrainer et al. |
| 7,464,706 B2 | 12/2008 | Steiner et al. |
| 8,172,817 B2 | 5/2012 | Michaels et al. |
| 2002/0101590 A1 | 8/2002 | Shimaoka |
| 2002/0144680 A1 | 10/2002 | Nilsson et al. |
| 2004/0163648 A1 | 8/2004 | Burton |
| 2004/0187869 A1 | 9/2004 | Bjorndal et al. |
| 2007/0006876 A1 | 1/2007 | Finlay et al. |
| 2007/0044793 A1* | 3/2007 | Kleinstreuer et al. ... 128/200.21 |
| 2007/0225587 A1* | 9/2007 | Burnell et al. ................. 600/407 |
| 2008/0015457 A1 | 1/2008 | Silva |
| 2008/0255468 A1 | 10/2008 | Derchak et al. |
| 2008/0319333 A1* | 12/2008 | Gavish et al. ................. 600/529 |
| 2009/0149727 A1 | 6/2009 | Truitt et al. |
| 2009/0151720 A1 | 6/2009 | Inoue et al. |
| 2009/0308391 A1 | 12/2009 | Smutney et al. |
| 2010/0235116 A1 | 9/2010 | Adamo et al. |
| 2010/0238457 A1 | 9/2010 | Adamo et al. |
| 2011/0000482 A1 | 1/2011 | Gumaste et al. |

FOREIGN PATENT DOCUMENTS

| | | | |
|---|---|---|---|
| WO | 2005/081977 A2 | 9/2005 | |
| WO | 2005/102428 A1 | 11/2005 | |
| WO | 2008/060484 A2 | 5/2008 | |
| WO | 2009/005546 A1 | 1/2009 | |
| WO | WO 2009005546 A1 * | 1/2009 | ............ A61M 15/00 |

OTHER PUBLICATIONS

Fadl et al., Effects of MDI spray angle on aerosol penetration efficiency through an oral airway cast. Journal of Aerosol Science, vol. 38, No. 8, pp. 853-864 (2007).
Sympatecs. Dry Dispersion for Laser Diffraction and Image Analysis, 2011. XP-002586530.
International Search Report mailed on Nov. 19, 2014 for International Application No. PCT/US2014/049817 filed on Aug. 5, 2014.
Gonzalez et al., Actualizacion del tratamiento farmacologico de la diabetes mellitus tipo 2. Del Sistema Nacional de Salud. Volumen 32, No. 1, pp. 3-16 (2008)—full article in Spanish with English abstract.
Skyler, Pulmonary insulin: current status. Diabetes Voice, vol. 51, Issue I, p. 23-25, 2006.
Wright et al., Inhaled Insulin: Breathing new life into diabetes therapy. Nursing, vol. 37, No. 1, p. 46-48 (2007).

* cited by examiner

APPARATUS AND METHOD FOR SIMULATING INHALATION EFFORTS

CROSS REFERENCE TO RELATED APPLICATIONS

This application claims benefit under 35 U.S.C. §119(e) from U.S. provisional patent application No. 61/257,813, filed on Nov. 3, 2009, the entire disclosure of which is incorporated herein by reference.

TECHNICAL FIELD

Described herein are an interactive apparatus and methods for recording, transferring and displaying key physical measurements based on physiological conditions generated by a subject during an inhalation maneuver, for instance, in real-time. In particular, the apparatus can be used alone and/or combined with an inhalation simulation system which can record and reproduce, or simulate a patient inhalation effort.

BACKGROUND

Inhaler devices for dispensing therapeutic substances via the respiratory tract, in particular, for pulmonary delivery in treating local or systemic diseases are commercially available. For example, nebulizers, devices containing propellants, and dry powder inhalers have been used for the treatment of diseases, such as asthma, respiratory tract infections and systemic disease such as diabetes.

The efficiency of delivering a required dosage of a therapeutic substance to a patient in treating a disease depends on the efficiency of the device, and overall delivery can be enhanced by providing proper feedback mechanisms to a patient during use of the device to teach, for example, proper inhalation techniques to a patient. Improper use of the devices and poor inhalation techniques can lead to lack of efficacy in treating a disease, for example, by administering lower dosages of a therapeutic substance than intended or higher dosages of a therapeutic substance which can be harmful to a patient. To effectively deliver therapeutic substances to the respiratory tract, a patient or user can be trained or coached to use the device in an appropriate manner.

Dry powder inhalers used to deliver medicaments to the lungs contain a dosing system for a powder formulation usually either in bulk supply or quantified into individual doses stored in unit dose compartments, like hard gelatin capsules, cartridges, or blister packs. Dosing reproducibility requires that the drug formulation is uniform and that the dose can be delivered to the patient with consistent and reproducible results. Therefore, dosing can be improved by optimizing discharge of a formulation, which is effectuated, for example, by having patients perform proper inhalation maneuvers.

Devices for training patients to properly deliver therapeutic substances by the pulmonary tract are described, for example, in U.S. Pat. No. 5,333,106, which discloses an apparatus for interactive training of a patient in use of an aerosol inhaler, including a feedback display based upon air flow versus volume data using a proper sequence of inhalation steps. Further, U.S. patent application Ser. No. 10/759,859 (Publication No. US 2004/0187869) discloses a training device for medicament inhalers, for example, dry powder inhalers, which is based on measuring pressure differential and displaying a single value corresponding to both inhalation rapidity and inhalation flow rate peak, and includes a dry powder inhaler simulator.

Dry powder inhaler and cartridge systems such as those describe in U.S. Pat. Nos. 7,305,986 and 7,464,706, the disclosures of which are incorporated herein by reference in their entirety for all they teach regarding dry powder inhalers, can generate primary drug particles or suitable inhalation plumes during an inspiratory maneuver by deagglomerating a powder formulation within the inhaler and capsule or cartridge. The benefits of delivering drugs via pulmonary circulation are numerous including rapid entry into arterial circulation, avoidance of first pass drug degradation by liver metabolism, and ease of use, for example, lack of discomfort compared to other routes of administration such as by injection. These devices have been in use in clinical settings and patients have been properly trained on the use of such inhalers.

There is a need in the art for improvements in design and manufacture of a device for training subjects in proper use of an inhalation system; monitoring patients during use of an inhalation system, monitoring the performance of an inhalation system, such as presence of leakage or defects, and capable of being coupled to a system for reproducing a patient's inhalation profile. The present disclosure presents apparatus and methods to achieve these goals.

SUMMARY

Described herein are apparatus for measuring key inspiratory characteristic parameters during use of an inhalation system. The apparatus and methods for using the apparatus can be useful, for example, in training and/or monitoring a subject requiring the use of an inhaler, for example, a high resistance, dry powder inhaler system for delivery of pharmaceuticals, active ingredients or medicaments to the lungs and pulmonary circulation. The apparatus can simultaneously measure and replicate the parameters of a patient's inhalation profile, or store the inhalation profile obtained and replicate the stored information at a later time.

Exemplary embodiments of the inhalation systems disclosed herein comprise a display means for visual cues to facilitate training and/or monitoring a subject in achieving an optimal or appropriate inspiratory or inhalation maneuver for the effective delivery of a therapy via the respiratory system. The system facilitates the training of subjects for the proper use of an inhalation device in order to achieve a preferred flow rate and/or pressure drop profiles for that individual so that maximal delivery of a medicament can be attained. The devices and methods can also be used to monitor inhalation systems performance, for example, detection of the dose being delivered; quantification of the drug being delivered, duration of discharge of a dose being delivered; number of doses administered to the subject, and to monitor the mechanical integrity of the inhalation system.

In an exemplary embodiment, the apparatus can perform interactively, for example, the apparatus comprises a wireless communication interface allowing remote acquisition of data, which can be sent to a computer/microprocessor based-system providing an interactive display of data, storage of data and/or web-based transfer of information. Alternatively, other exemplary embodiments can comprise a wired communication interface.

In one exemplary embodiment, the apparatus or device can be adapted, for example, to a high resistance dry powder inhalation system, such as those described in U.S. Pat. Nos. 7,305,986 and 7,464,706, and U.S. patent application Ser. Nos. 12/413,405 and 12/484,125; the disclosures all of which are incorporated herein by reference in their entirety for all they disclose regarding dry powder inhalers. However, any type of inhaler can be used. The device can comprise an inhaler with or without a cartridge containing a pharmaceutical formulation, one or more transducers including, electrical, electronic, electro-mechanical, electromagnetic, photonic or photovoltaic; such as pressure sensors, temperature sensors, electroacoustic or sound sensors, and optical sensors; a signal conditioning circuitry and/or a software program, a means for electronic signal communication and an output display. In such an exemplary embodiment, the apparatus can be used with an analog or digital sensor, appropriate signal conditioners such as amplification, signal filtering, analog to digital conversion, a microprocessor for onboard processing, a wireless communicator in communication with a remote computer or personal data assistant (PDA) for subsequent signal processing and/or real-time output display. The device can be used to deliver pharmaceutical compositions housed in pre-metered unit dose cartridges containing an active ingredient for delivering to the pulmonary circulation. In alternative exemplary embodiments, the sensing and monitoring device can be adapted onto or within an inhalation system comprising a dry powder inhaler with a cartridge that can be empty, or can contain a dry powder suitable for pulmonary delivery.

In one embodiment, the apparatus can be used to deliver the measured parameters to a system which recreates a patient's measured profile and which system can recreate or simulate a patient's inhalation maneuver at the same time as the patient inhales or at a later time. In this embodiment, the simulation inhalation system includes a computer with a microprocessor and a set of machine-readable instructions that are executable by a processing device to implement an algorithm, wherein the algorithm comprises instructions for manipulating the data including the steps of: receiving the data from at least one sensor; filtering the data; transforming the data; analyzing the data; and displaying a patient's stored information profile. In a particular embodiment, the algorithm activates the motor controller to actuate a syringe pump creating a vacuum thereby simulating a subject's inhalation. In one embodiment, the apparatus for reproducing a patient's inhalation profiles comprises a closed loop system that automatically produces pressure drop, volume and flow measurements in a controlled chamber, which resultant pressure drop and flow rate produced evacuates a powder contained in an inhaler adapted to the system using an anatomical model having an artificial substantially accurate upper respiratory tract or airway. In one embodiment, the apparatus can replicate previously measured inhalation profiles from a subject enabling characterization of inhalation parameters, including, peak inspiratory pressure, pressure increase rate or speed at which the pressure is changing, volume, and time to peak pressure or flow rate.

Dry powders comprising microparticles suitable for pulmonary delivery are well known in the art including, for example, those disclosed in U.S. Pat. Nos. 6,428,771 and 6,071,497, the disclosures of which are incorporated herein by reference in their entirety for all they disclose regarding microparticles. In respective exemplary embodiments, the dry powders, the active ingredient can be a protein, a peptide, or a polypeptide and combinations thereof, for example, and endocrine hormone such as insulin, glucagon-like peptide-1 (GLP-1), parathyroid hormone or analogs thereof.

In certain embodiments, a dry powder formulation for delivery to the pulmonary circulation comprises an active ingredient or agent, including a peptide, a protein, a hormone, analogs thereof or combinations thereof, wherein the active ingredient is insulin, calcitonin, growth hormone, erythropoietin, granulocyte macrophage colony stimulating factor (GM-CSF), chorionic gonadotropin releasing factor, luteinizing releasing hormone, follicle stimulating hormone (FSH), vasoactive intestinal peptide, parathyroid hormone (including black bear PTH), parathyroid hormone related protein, glucagon-like peptide-1 (GLP-1), exendin, oxyntomodulin, peptide YY, triptans such as sumatriptan, interleukin 2-inducible tyrosine kinase, Bruton's tyrosine kinase (BTK), inositol-requiring kinase 1 (IRE1), or analogs, active fragments, PC-DAC-modified derivatives, or O-glycosylated forms thereof. In particular embodiments, the pharmaceutical composition or dry powder formulation comprises fumaryl diketopiperazine and the active ingredient is one or more selected from insulin, parathyroid hormone 1-34, GLP-1, oxyntomodulin, peptide YY, heparin, PTHrP, analogs thereof and combinations thereof.

In one exemplary embodiment described herein are dry powder inhalers comprising: a sensor in communication with the dry powder inhaler, wherein the sensor can detect at least one signal type, including pressure, temperature, and acoustic or sound signals generated from the dry powder inhalation system, and the sensors can send signals to at least one device for analysis, storage, printing or display, including in real-time. In such an exemplary embodiment, the sensor is configured within the dry powder inhaler or adaptable to the dry powder inhaler and the sensor can be a microphone.

In an exemplary embodiments, the inhalation systems comprise a dry powder inhaler having high resistance to airflow and a resistance value between about 0.065 ($\sqrt{kPa}$)/liter per minute and about 0.200 ($\sqrt{kPa}$)/liter per minute. High resistance inhalation systems can be provided with the sensing and monitoring apparatus described herein, although low resistance or other types of inhalers can also be adapted with the present system. In one embodiment, the sensor can detect intrinsic characteristic signals generated by the inhalation system in use. In another exemplary embodiment, the sensor is a sound sensor which includes a sound detecting device or a microphone, configured to transmit the sound signal by wire or wireless communication mode to at least one other device in the system. The sensing and monitoring apparatus for dry powder inhalers described herein can further be associated with an analog to digital converter which communicates at least one signal such as a sound signal to a microprocessor configured to analyze and process the signal. In another exemplary embodiment, at least one device is an analog to digital converter.

In one exemplary embodiment, monitoring systems are described for a dry powder inhaler comprising: a monitoring device comprising at least one sensor; an analog to digital converter; a data storage medium, wherein the data storage medium includes a set of machine-readable instructions that are executable by a processing device to implement an algorithm, wherein the algorithm comprises instructions for manipulating and analyzing data including the steps of: receiving the data from at least one sensor; filtering the data; transforming the data; analyzing the data; and monitoring a patient using the data obtained.

In an exemplary embodiment wherein at least one sensor is a microphone, the monitoring device is provided any place within the inhaler, for example, within the airflow conduits, within the wall of the inhaler, or outside of the inhaler as a separate piece. In another exemplary embodiment, the monitoring device can also be a detachable device that can be configured to be mounted on, or attachable to the inhaler, for example, a jacket or similar structure for adapting dry powder inhaler. In yet another exemplary embodiment, the monitoring device provides a graphical display which is a real-time graphical representation of an inhalation performed by a subject using the device.

In another exemplary embodiment, the signal is an amplitude of sound signal, a frequency of sound signal or combinations thereof. In yet other exemplary embodiments, the sensor further measures at least one sound signal at different frequencies. In another exemplary embodiment, the dry powder inhalers further comprise a cartridge and the cartridge can comprise a dry powder for pulmonary delivery. In one embodiment, the dry powder can comprise, for example diketopiperazine microparticles, including, substituted-diketopiperazine microparticles, for example, fumaryl diketopiperazine, and at least one active ingredient. In still another embodiment, at least one medicament comprises insulin, GLP-1, parathyroid hormone, sumatriptan, calcitonin, analogs thereof, or combinations thereof.

In a further embodiment, the sensing and/or monitoring device is configured to detect signals from a dose being delivered to a subject. In this embodiment, the sensing and monitoring system can detect movement of particles, for example, powder particles within the inhaler and optionally, within a cartridge system in use, from initiation of powder delivery to the end of delivery of the powder particles, wherein the sensor detects variations in the intrinsic characteristics of inhaler sound and powder particles sound emanating from the inhalation system. Data obtained from the detection recordings can be analyzed and correlated to the amount of dose emitted or delivered out of the inhalation system, the time that elapsed for dose delivery, and the performance of the inhalation system.

In another exemplary embodiment, the sensing and monitoring apparatus can be provided as an adaptable, detachable device such as a jacket, saddle, or any structure that can be adapted to an inhaler, including, dry powder inhalers. In this embodiment, the removable device facilitates use of the inhalation system, since the structure or configuration and operation of the inhaler is not modified or compromised. Therefore, the same inhaler can be used without the jacket once the characteristic performance of the inhaler has been determined and the subject can properly use it. In embodiments herein, the sensor, such as a small microphone, can be advantageously placed in any area of the jacket, including, for example, embedded in the wall of the jacket or adaptor, or extending from the walls of the jacket. In this embodiment, the sensing and monitoring apparatus offers greater resolution of sound characteristics emanating from the inhaler and cartridge system in use.

In one exemplary embodiment, methods are described for measuring pressure differential during an inhalation maneuver, the method comprises: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal and said at least one frequency of sound signal, or combinations thereof using an algorithm provided with a microprocessor in a computer system to generate a data set; and displaying, printing, or storing the data set as a function of time and pressure.

In further exemplary embodiments described herein are monitoring systems for use with dry powder inhalers comprising: a monitoring device having at least one sensor; an analog to digital converter; a data storage medium, wherein the data storage medium includes a set of machine-readable instructions that are executable by a processing device to implement an algorithm, the algorithm comprising instructions for manipulating or processing data including the steps of: receiving the data from the at least one sensor during an inhalation by a patient; filtering the data; transforming the data; analyzing the data; displaying the data obtained and monitoring a patient inhalation using the data.

Even further still, in one embodiment described herein are methods for measuring pressure differential during an inhalation maneuver, comprising: providing an inhaler to a subject wherein the inhaler comprises a sensor configured to detect at least one amplitude of sound signal, at least one frequency of sound signal or combinations thereof generated from the inhaler, having the subject inhale for at least one second; analyzing the at least one amplitude of sound signal, the at least one frequency of sound signal, or combinations thereof using an algorithm provided with a computer system to generate a data set; and displaying, printing, or storing the data set as a function of time and pressure.

In other embodiments described herein are interactive dry powder inhalation systems for monitoring an inhalation performed by a user, comprising: a dry powder inhaler comprising a cartridge and having a resistance to flow values between 0.065 ($\sqrt{kPa}$)/liter per minute and 0.200 ($\sqrt{kPa}$)/liter per minute; a transducer configured to detect a signal generated from the inhaler in use, and a display device configured to display in real-time an inhalation maneuver performed by a user. In another embodiment, the transducer senses and measures a pressure differential within the inhaler. Further still, the transducer can be a flow meter configured to detect and measure flow rate through air conduits of the dry powder inhaler. The transducer can be, for example, an electroacoustic device such as a microphone configured to detect and measure a sound signal generated from within the inhaler.

In still other embodiments described herein are sensing and monitoring devices for adapting to an inhaler such as a dry powder inhaler, comprising: a detachable device structurally configured to adapt to a dry powder inhaler; the detachable device comprising a microphone for detecting sound generated in the inhaler; and wherein the dry powder inhaler has a resistance to flow value between 0.065 ($\sqrt{kPa}$)/liter per minute and 0.200 ($\sqrt{kPa}$)/liter per minute.

Further, in one embodiment, sensing and monitoring devices are described for a dry powder inhalation system, wherein the dry powder inhalation system comprises a dry powder inhaler and a cartridge, and the sensing and monitoring device comprises a microphone configured to detect sound signals generated from a dry powder formulation emitted from the dry powder inhalation system.

In another embodiment, the sensing and monitoring devices described herein are combined with a simulating module that can generate a pressure differential such as a syringe pump, in a closed loop system. The simulating module can communicate via signals with a computer having a microprocessor with instructions for regulating or controlling the syringe pump to generate or create a desired vacuum or pressure drop to recreate a person's inhalation profile for a predetermined time of inhalation execution. In this embodiment, inhalation profiles obtained from a subject can be stored by the system and recreated or simulated in vitro to assess and determine the subject's effort needed to deliver a required dose with an inhaler. In this embodiment and other embodiments, the simulating module further comprises a substantially accurate anatomical head configured to have a mouth configured to receive an inhaler and has a substantially accurate model of a respiratory tract, for example, the benhead, which is configured to be adaptable and attachable to a connecting structure, including a cylinder or tube connected to a syringe pump. In this and other embodiments, the substantially accurate anatomical head can further be configured to adapt an artificial lungs device or a filtration device for trapping a powder dose during use of the simulating module.

In an exemplary embodiment, a dry powder inhalation simulation system is provided comprising: a dry powder inhaler; a sensor in communication with the dry powder inhaler; the sensor is configured to detect at least one type of signal generated from the powder inhaler and transmit at least one type of signal to at least one device for analysis, storage, printing and/or display; an artificial anatomical head comprising a substantially accurate upper respiratory tract including a mouth; a calibration syringe pump; a power supply; a computer comprising a microprocessor, an algorithm and a display monitor.

A method for simulating an inhalation maneuver by a subject is also provided, comprising providing a subject with a first inhaler adapted with a wireless or wired first sensor and a first radio transmitter; having the subject inhale through the first inhaler to produce a pressure differential through the first inhaler or an inhalation; wherein the subject can be positioned nearby an inhalation simulation apparatus comprising a computer with a microprocessor comprising a signal receiver and an algorithm configured to analyze and process the signal produced from the first sensor and generate a set of data that can be stored and/or simultaneously used by the computer; a motor controller, a motor, a vacuum source such as a calibrated syringe pump, and an artificial substantially accurate anatomical upper respiratory airway, and a second inhaler comprises a wired or wireless second sensor, a second radio transmitter and optionally, a dry powder formulation; collecting at least one type of signal from flow generated in the first inhaler; converting the signal to a set of data from the subject's inhalation provided by the first sensor in the computer or microprocessor with the algorithm; and generating a second set of signals in the computer to instruct the controller to activate the motor to move the syringe pump to generate a pressure differential equal to the pressure differential generated by the subject's inhalation.

In other embodiments, the simulation system is provided with an inhaler of the same type provided to a subject and comprising a sensor adapted to the inhaler and a powder formulation comprising a drug; wherein the inhaler is adapted to the artificial substantially accurate anatomical upper respiratory airway and configured to deliver the powder formulation to the artificial substantially accurate anatomical upper respiratory airway which can be connected to a clear, see through cylinder for assessing or determining the powder properties delivered by the inhaler prior to dosing a subject with the inhaler. In this manner, inhaler delivery efficiency can be assessed for individual subjects.

DETAILED DESCRIPTION

Figure 1:
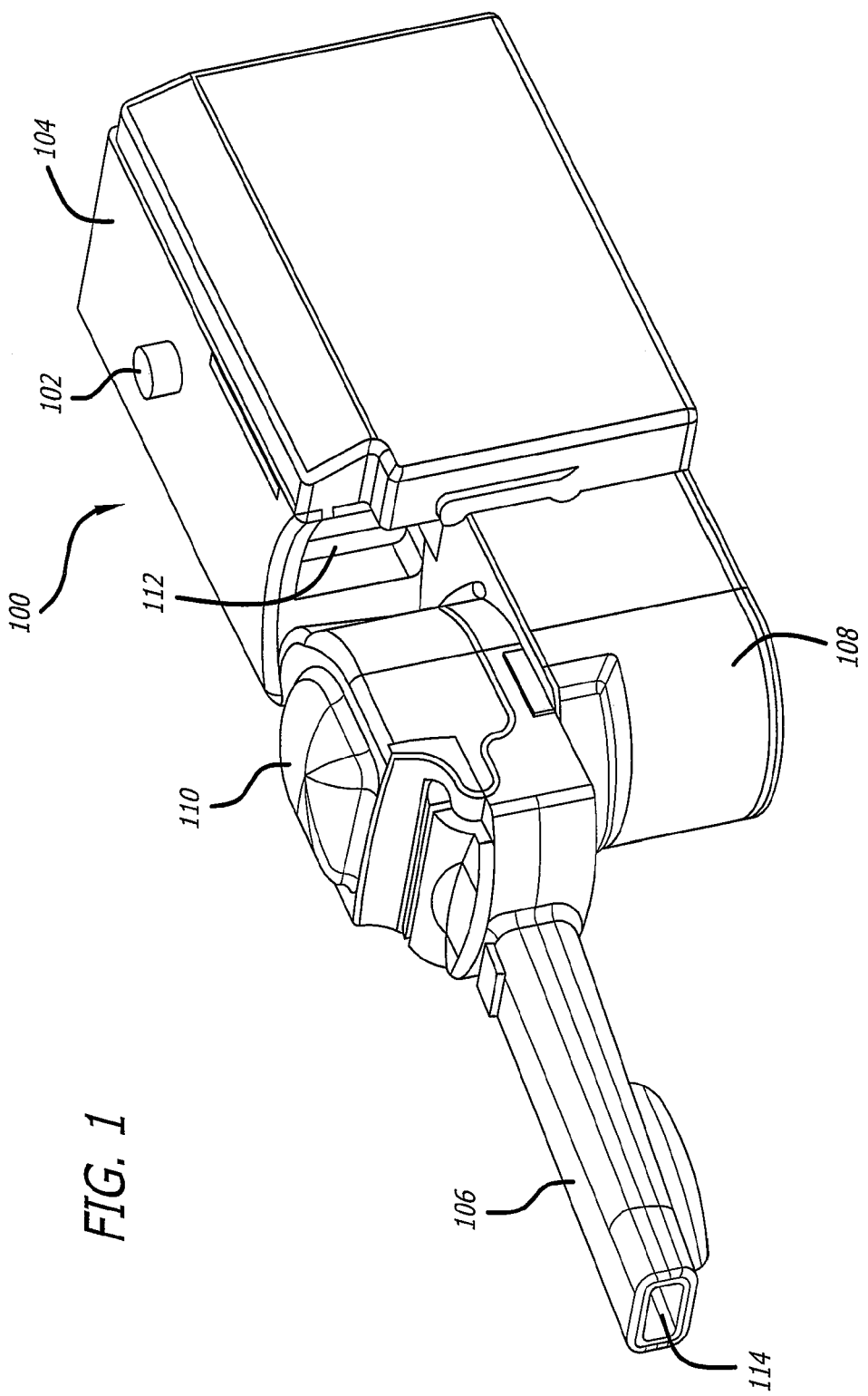
FIG. 1 illustrates an isometric view of the right side of an embodiment of a dry powder inhaler training apparatus.

Disclosed herein are inhalation simulation systems and methods for using the systems for various applications. In an exemplary embodiment, the inhalation simulation system is a closed loop system comprising two components: a first component comprising an inhalation apparatus comprising an inhaler, and an interactive system which measures or monitors changes in pressure or pressure drop and/or flow rate characteristics from a subject during an inhalation maneuver, and a second component, which receives and converts the information such as an inhalation profile obtained from a subject's inhalation using the first component data, and recreates the information to replicate the patient inhalation in vitro.

In particular embodiments described herein, the first inhalation apparatus comprises and inhaler and an interactive system configured to detect or sense, and output information obtained during an inhalation in real-time or substantially instantaneously as the subject inhales, which information or data can be stored and/or displayed simultaneously as the information is obtained. The inhalation apparatus can be used for training a subject to maximize efficiency of their respiratory maneuvers in conjunction with an inhalation device, and can also be used for monitoring inhalation during delivery of a medicament to detect proper dose delivery, timing of dose delivery and proper performance of the inhaler in use. In one exemplary embodiment, the sensing and monitoring apparatus can be used with any inhaler type. However, in particular embodiments describe herein, the system can be applied in conjunction with a high resistance inhaler, including dry powder inhalers.

The inhalation apparatus comprises a transducer or sensor which can convert at least one measurand, including, pressure, air flow, air volume, humidity, and temperature, to an electrical signal. The device further includes appropriate signal conditioning circuitry, such as signal filtering, amplification and analog to digital conversion, and processing circuitry such as a microprocessor, wired or wireless communication interface and the like to transfer the generated signal in real-time to a receiving computer or personal data assistant (PDA) for display of the signal. In one embodiment, the output display can be an interactive display so that the display device provides a visual aid for teaching a subject to perform repeatable inhalation maneuvers in real-time, thereby facilitating proper inhalation delivery of medicament. In another exemplary embodiment, the data can be stored to be analyzed at a later time, or used in other applications.

In one embodiment, the sensing and monitoring can be adapted to transmit signals to or communicate with an inhalation simulating device comprising a chamber, a vacuum source such as a syringe pump or piston driven device which can generate pressure differentials and/or flow rates through the chamber. The syringe pump can comprise a microprocessor which can be actuated by signals from a computer which can be transmitted wireless or wired to a controller. Computer signals can be generated from a subject's inhalation profile which is being analyzed by an algorithm simultaneously during an inhalation maneuver, or from information obtained from a subject's inhalation profile stored in the computer system components.

FIGS. 1 through 4 illustrate an exemplary inhalation apparatus comprising a dry powder inhaler training device. The training device describe herein comprises an interactive system adapted to a high resistance dry powder inhaler as disclosed in U.S. Pat. Nos. 7,305,986 and 7,464,706, U.S. patent application Ser. No. 11/934,643 (US 2008/0053437), Ser. No. 11/949,707 (US 2008/0127970), Ser. No. 12/102,625; and other high resistance dry powder inhalers are disclosed in U.S. patent application Ser. Nos. 12/413,405; 12/484,125, the disclosures each of which are incorporated herein by reference herein for all they disclose regarding dry powder inhalers.

Figure 2:
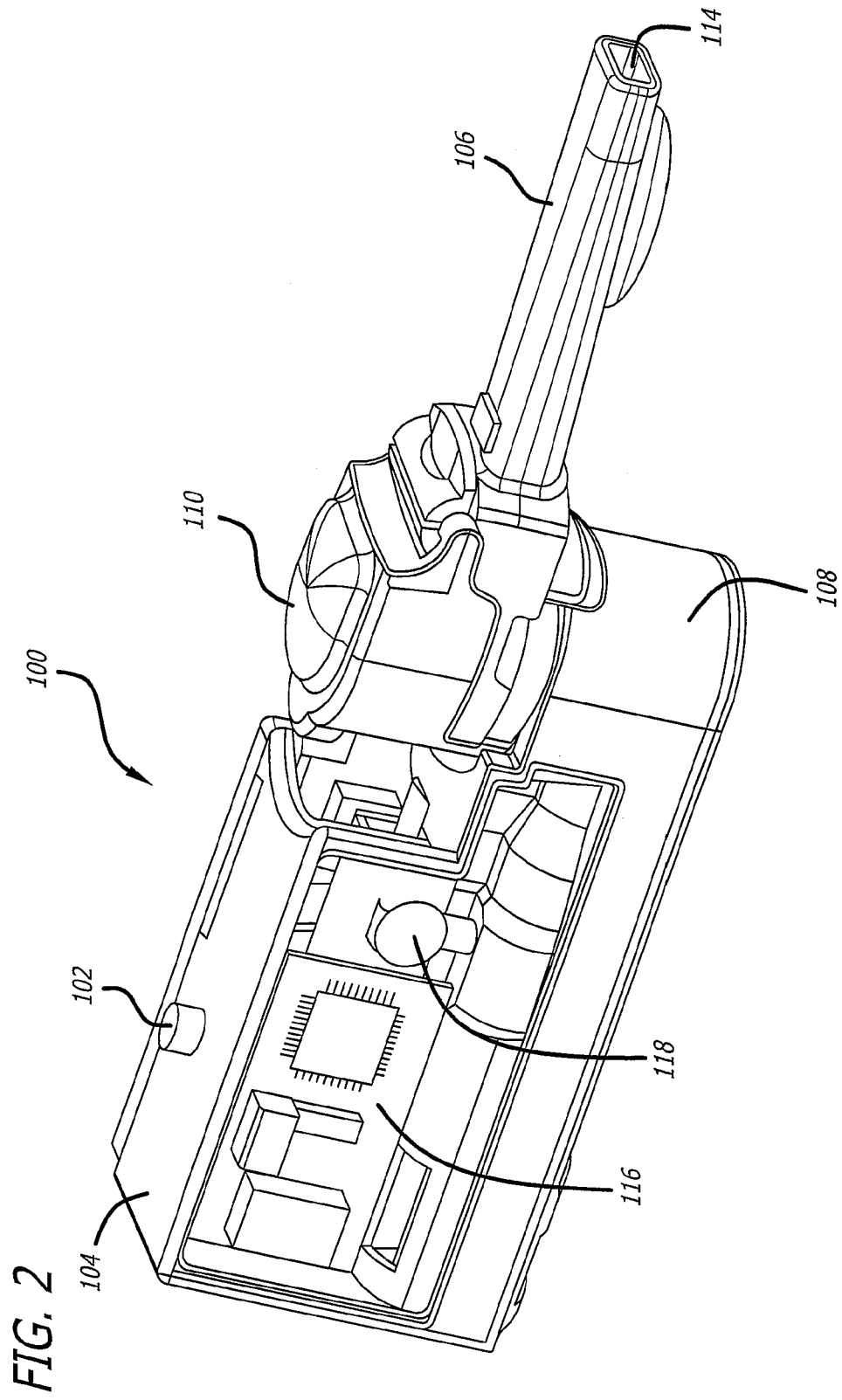
FIG. 2 illustrates an isometric view of the left side of the embodiment of FIG. 1, wherein part of the housing has been removed to show internal component parts of the dry powder inhaler training device.
Figure 3:
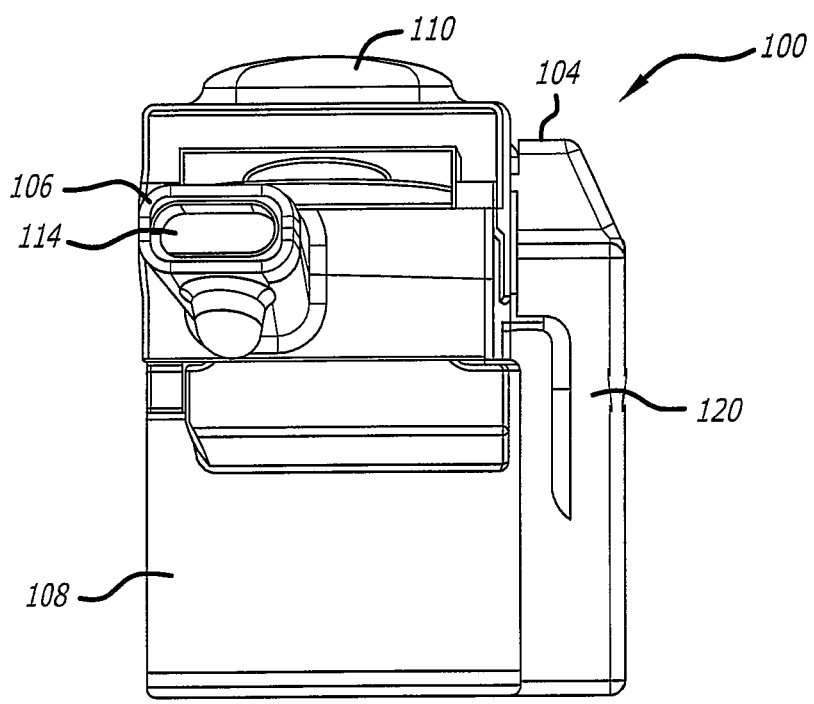
FIG. 3 illustrates a back view of the embodiment of FIG. 1.

Training device 100 comprises activator button 102, housing 104, mouthpiece 106, mixing section 108, a cap or lid 110 over mixing section 108, air inlet port 112 and air outlet port 114. An air conduit is established between air inlet port 112 and air outlet port 114. FIG. 2 illustrates training device 100 with left panel (not shown) of housing 104 removed showing the position of signal processing/interface board 116 and sensor 118 within housing 104. FIG. 3 illustrates a back view of training device 100 showing housing 104 having a compartment with cover 120 on the right side for accommodating a power source.

Figure 4:
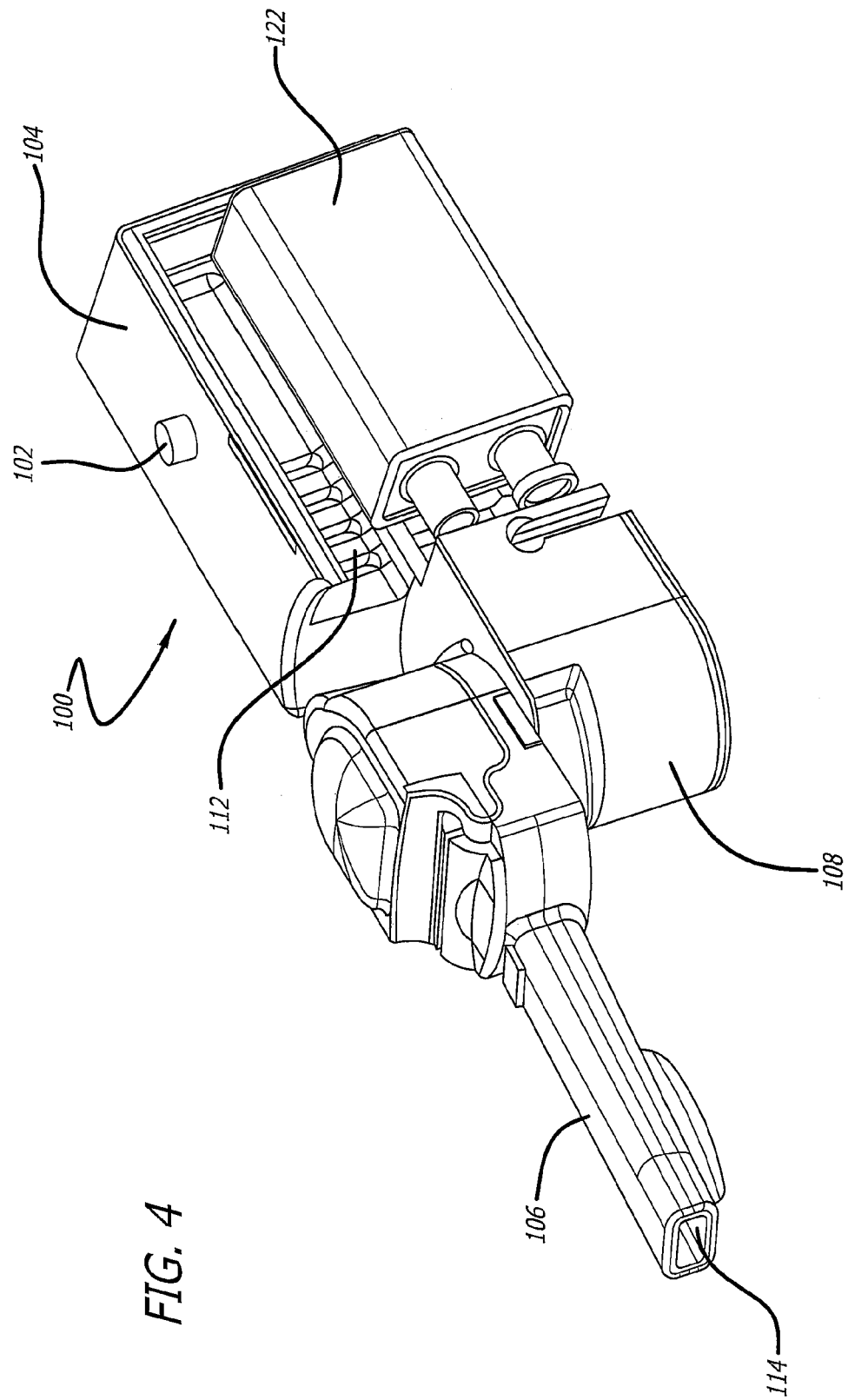
FIG. 4 illustrates an isometric view of the right side of the embodiment of FIG. 1 with the device cover removed to show additional component parts in the interior of the device.

In one exemplary embodiment, sensor 118, in an analogue form, is placed within housing 104 and detects pressure differential from training device 100 when training device 100 is turned on by depressing activator button 102 which is connected to a power source, such battery 122 illustrated in FIG. 4, that also provides power to the system. Sensor 118 can be placed at any point within the air conduit of training device 100. In some exemplary embodiments, sensor 118 can be placed in the air conduit within housing 104. In other exemplary embodiments, sensor 118 can be placed within the mixing chamber (not shown) or the air conduit of mouthpiece 106.

Figure 5:
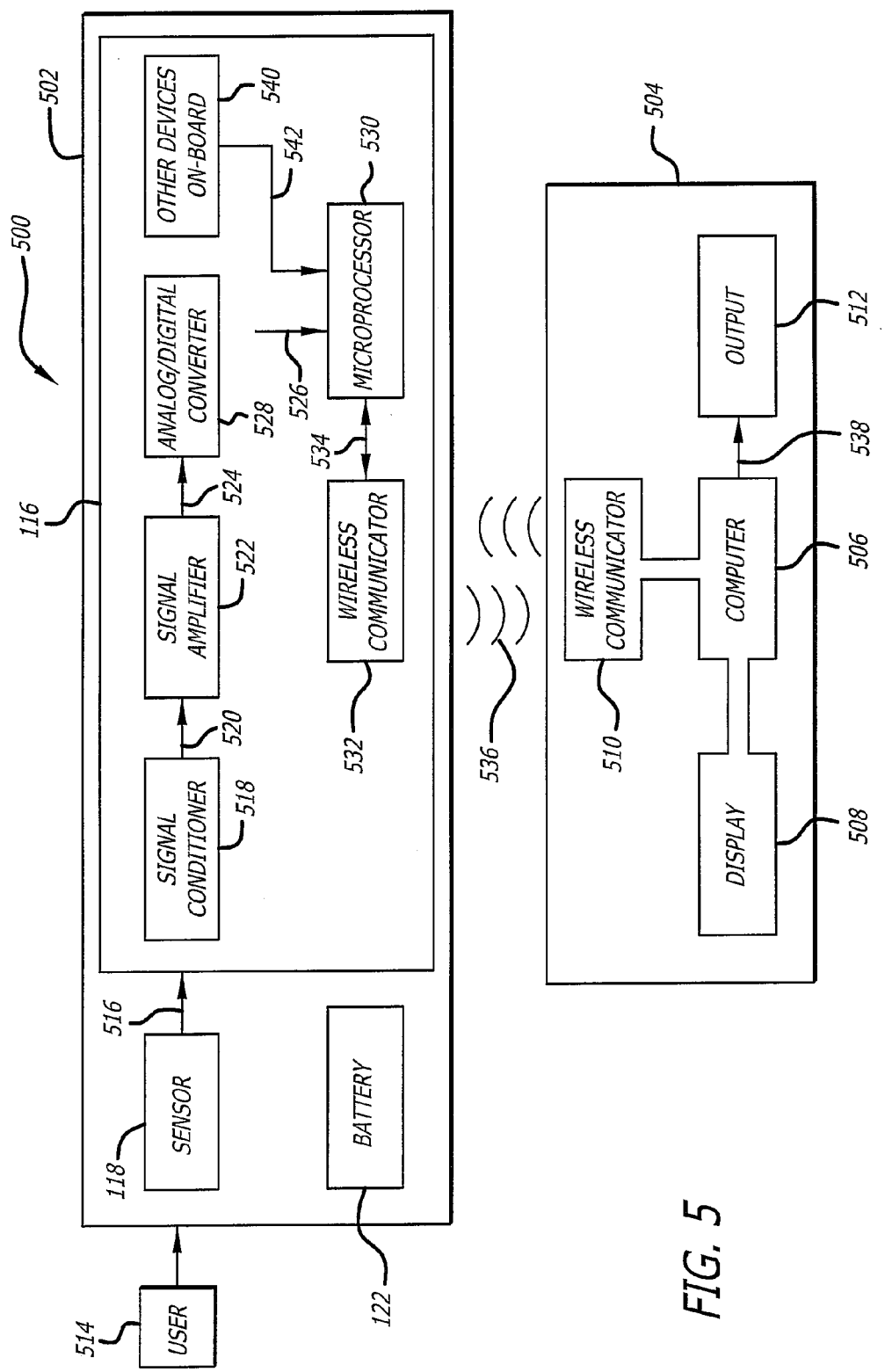
FIG. 5 illustrates a block diagram of the overall training system disclosed herein.

FIG. 5 illustrates a block diagram for an inhalation apparatus, such as training device 100, showing its various operational component parts. In FIG. 5, system 500 comprises two components, inhaler training device 502 and processing system 504. Processing system 504 can include a PDA or computer 506, display 508, wireless communicator 510 and output 512 which can be in the form of digital storage, a web interface, a print out or the like. In this exemplary embodiment, a user can activate inhaler training device 502 by depressing a power button, for example button 102 on training device 100, with processing system 504 also activated. When the software program integrated with computer 506 is ready, a start signal appears on display 508. With the system activated, inhalation 514 generates a pressure drop in inhaler training device 502 which is transduced to an electrical signal by sensor 118. In this embodiment, the sensor 118 can be a pressure, flow, sound, optical, gas, humidity, or temperature transducer that is either analogue or digital. Electrical signal 516 from sensor 118 is then transmitted to signal conditioner 518 to remove unwanted signals, such as signal noise. Conditioned electrical signal 520 is then transmitted to signal amplifier 522 wherein conditioned electrical signal 518 can be amplified to a predetermined voltage range, and transmitted as amplified signal 524. Amplified signal 524 is then converted to digital signal 526 through analog to digital converter 528. Digital signal 526 then passes through microprocessor 530 and into second wireless communicator 532 through connection 534 for transmission to computer 506, having wireless communicator 510 for receiving wireless signal 536. A software program built into/programmed into microprocessor 530 or computer 506 converts electrical signal 516 to a pressure value which can be displayed graphically. In certain embodiments, a baseline curve for inhaler training device 502 is provided as a reference standard to guide the user's inhalation maneuver. Therefore, during an inhalation, a user can visually compare his/her inhalation maneuver to the baseline standard. In this manner, the user can alter his/her inhalation effort to conform to the requirements of the standard. The displayed data for each inhalation performed by a subject can be saved via second connection 538 to output 512 wherein the data can be stored or transferred accordingly. For example, output 512 can be in the form of a flash drive or printer, or transmitted via email to a physician for review or further training as needed. In one embodiment, signals from the inhalation training device can be transmitted to the computer/PDA and signals from the computer/PDA can be received by the inhalation training device, thereby establishing a two way communication between the two components.

Further, other on-board devices 540 can send and receive data from microprocessor 530 through one or more cable 542. For example, other on-board devices can include digital output sensors, temperature sensors, light emitting diodes (LEDs), sound warning devices, and other on-board sensors.

Other configurations of block diagram 500 can also be configured, for example, following the signal amplification amplified signal 524 can be directly sent to computer 506 via second wireless communicator 532 and the computer can do the analog to digital conversion and other required analysis steps.

Figure 6:
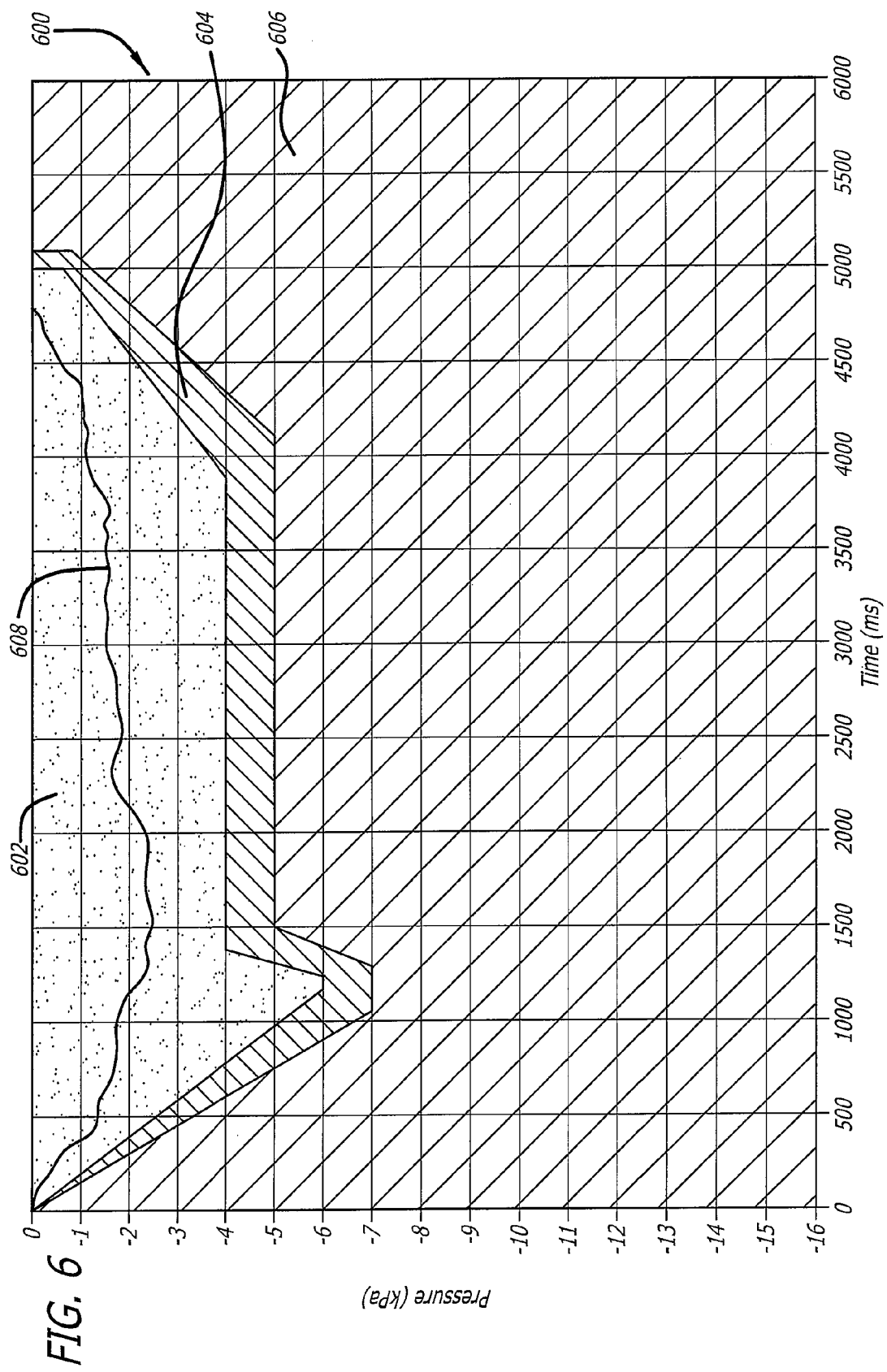
FIG. 6 graphically illustrates an inhalation maneuver performed by a subject without coaching.
Figure 7:
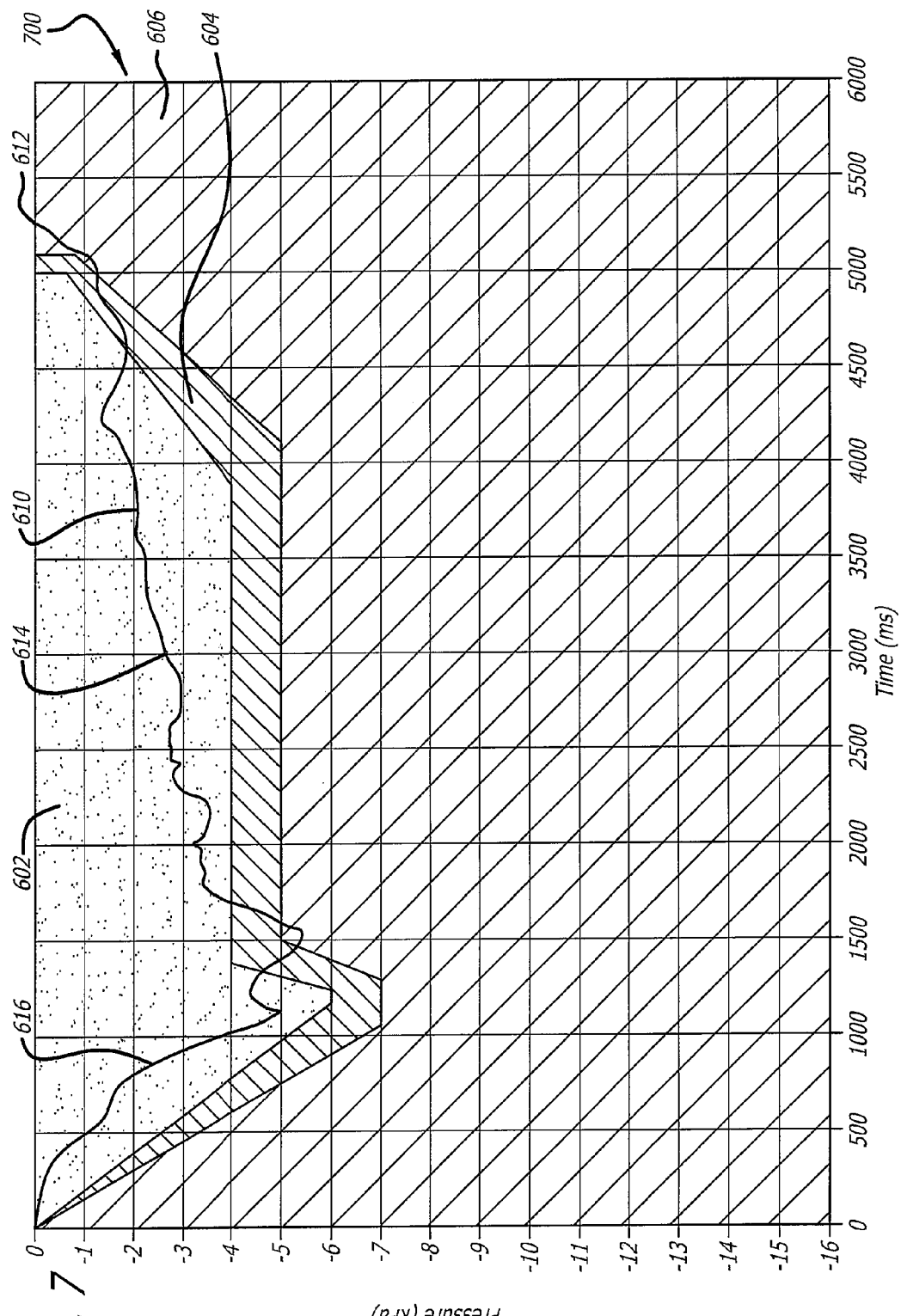
FIG. 7 graphically illustrates an inhalation maneuver performed by a subject only coached to take a deep breath.
Figure 8:
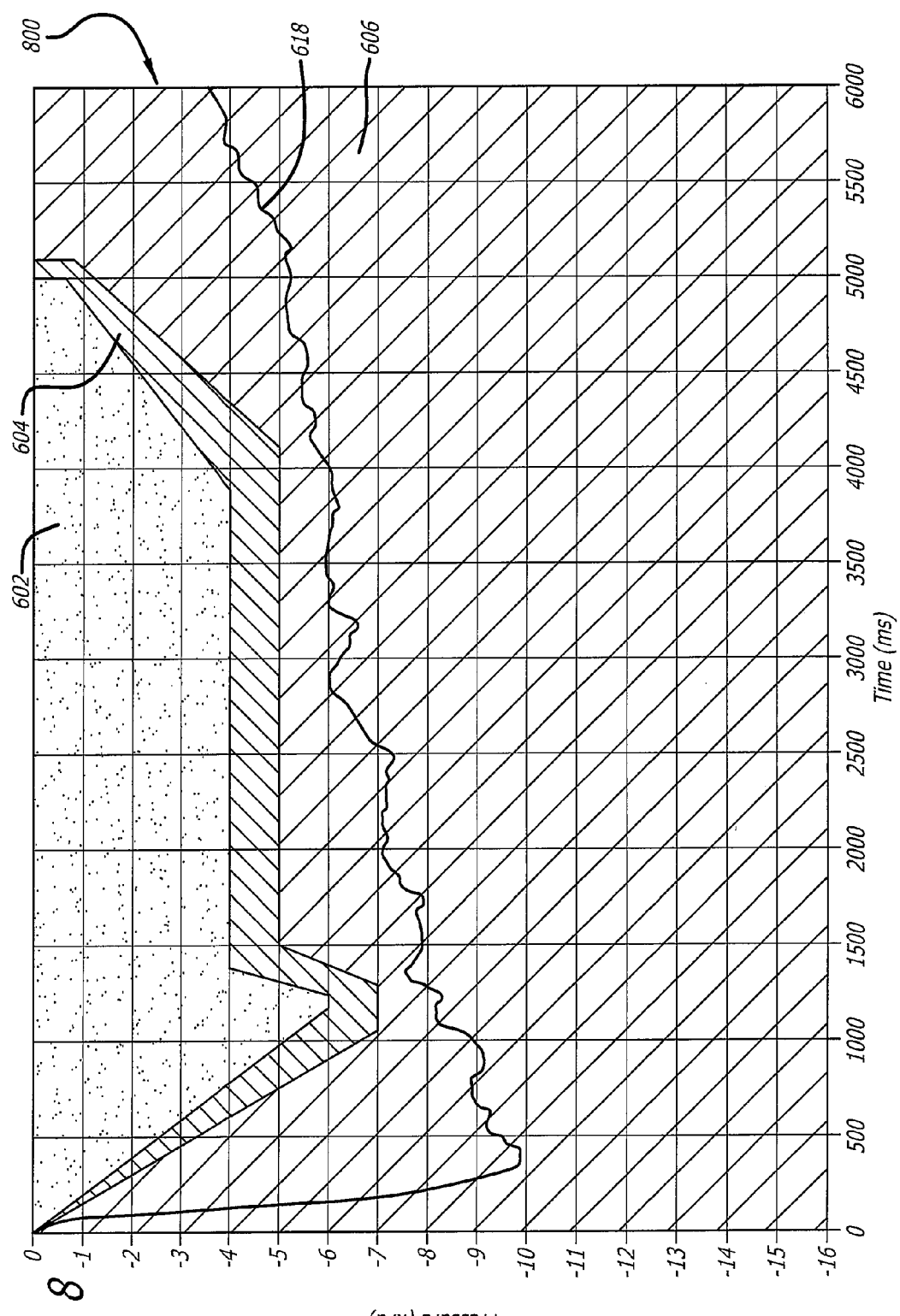
FIG. 8 graphically illustrates an inhalation maneuver performed by a subject properly trained to use a dry powder inhaler using the training device.

Exemplary data from training sessions with a subject are illustrated in FIGS. 6 through 8. Each figure depicts a graph (600, 700, 800) of data displayed by the training systems described herein after an inhalation maneuver. The graphs are plotted as pressure in kilopascals (kPa) on the y-axis and time in milliseconds on the x-axis. A baseline inhalation performance standard for training device 100 is shown as region 602 which is bordered by a warning region 604 and an acceptable or preferred region 606. Regions 602, 604 and 606 can be provided in different colors facilitating discernment of regions in monitoring an individual's performance during an inhalation. Region 602 can be, for example, depicted in red, indicating that the inhalation maneuver did not meet the baseline requirement. Therefore, the delivery system would not be optimal to deliver a medicament effectively. Warning region 604 can be depicted in yellow indicating a warning that the inhalation maneuver is nearing the unacceptable performance effort. Preferred region 606 can be depicted in green indicating that the inhalation performance is in the acceptable efforts to effectively deliver a medicament.

FIG. 6 graphically illustrates an example of an inhalation maneuver performed by a subject who has received no training and is not allowed to see the screen display of the computer during the inhalation maneuver. The results of this inhalation are plotted as curve 608. As graphically illustrated in FIG. 6, the inhalation effort by the subject falls in the unacceptable region 602 during the entire inhalation procedure.

FIG. 7 graphically illustrates results of an inhalation maneuver of a subject who has received some guidance on the use of a device and is allowed to look at a computer screen displaying the inhalation effort during the maneuver. In this maneuver and as shown by curve 610, the subject inhaled for an acceptable period of time, as indicated by end point 612 falling within preferred region 606, but did not inhale quickly enough or with enough effort to attain acceptable values, as indicated by regions 614 and 616 which fall within region 602.

FIG. 8 graphically illustrates an example of an inhalation maneuver performed by a subject who has received complete training and is allowed to see the display screen on a computer while performing the inhalation. As can be seen by curve 618, the subject performed entirely within acceptable values in region 606.

The graphs illustrated in FIGS. 6-9 and 19 can be incorporated into a computer program and captured as a screenshot therefrom. Other features of the devices and systems described herein can be controlled using a computer or microprocessor and visualized through an onscreen display.

In some exemplary embodiments disclosed herein, one or more key parameters can define an acceptable inhalation maneuver, including, total inhalation time, peak inspiratory pressure, time to peak inspiratory pressure and average pressure from peak to about 75% of the total inhalation time. In certain embodiments, the total inhalation time can be greater than 5 seconds, the peak inspiratory pressure can be greater than about 6 kPa, time to peak inspiratory pressure can be less than about 1.1 seconds and the average pressure from peak inhalation to 75% of total inhalation time is about 4 kPa. These values are representative of values for training device 100, and can be modified for alternate inhaler training devices, depending on the performance parameters required for optimal delivery of the medicament of the inhaler, including resistance.

Figure 9A:
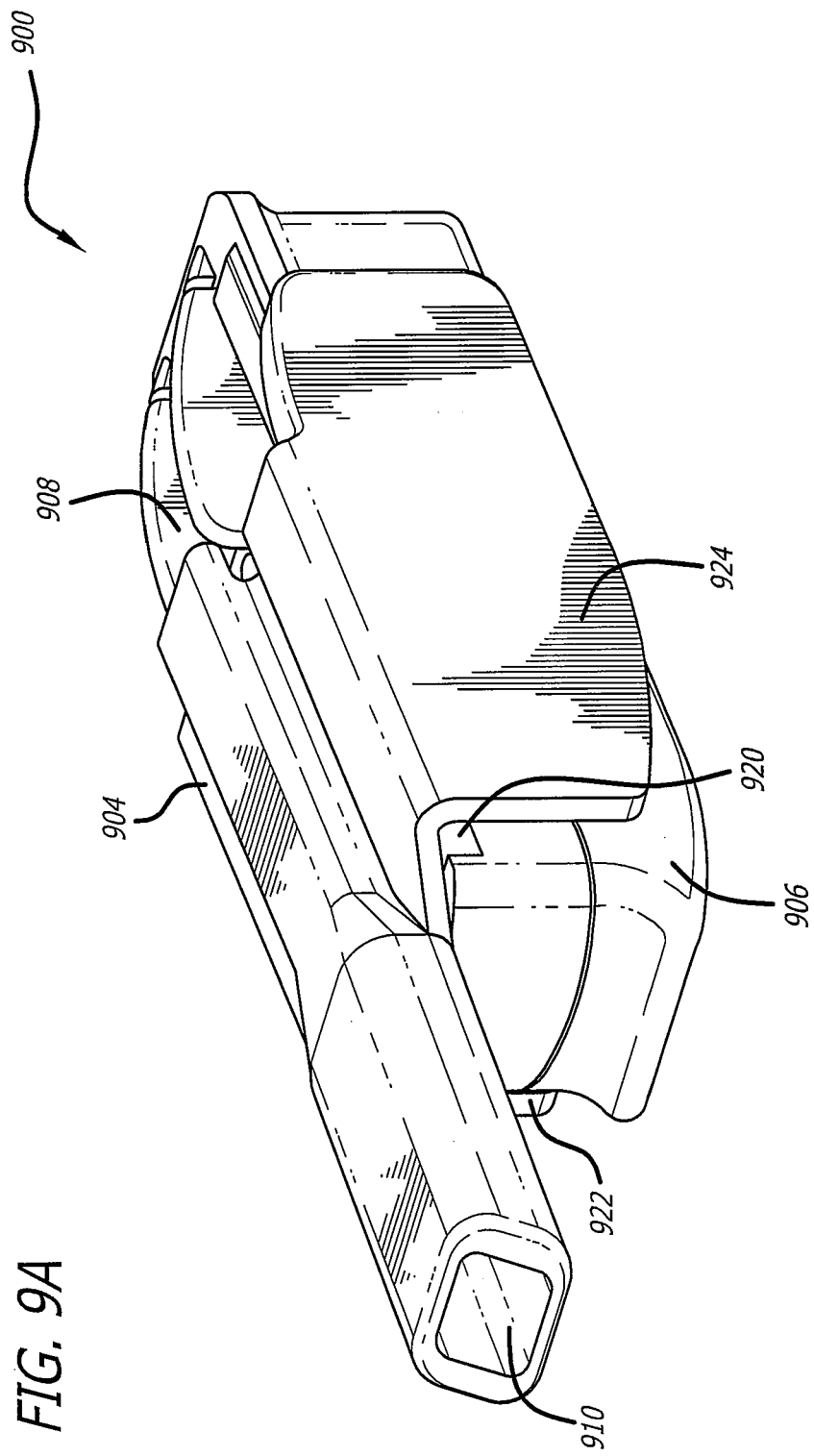
FIGS. 9A and 9B illustrate isometric views of an alternate embodiment of an inhaler with (9B) and without (9A) an integrated sensing and monitoring device.
Figure 9B:
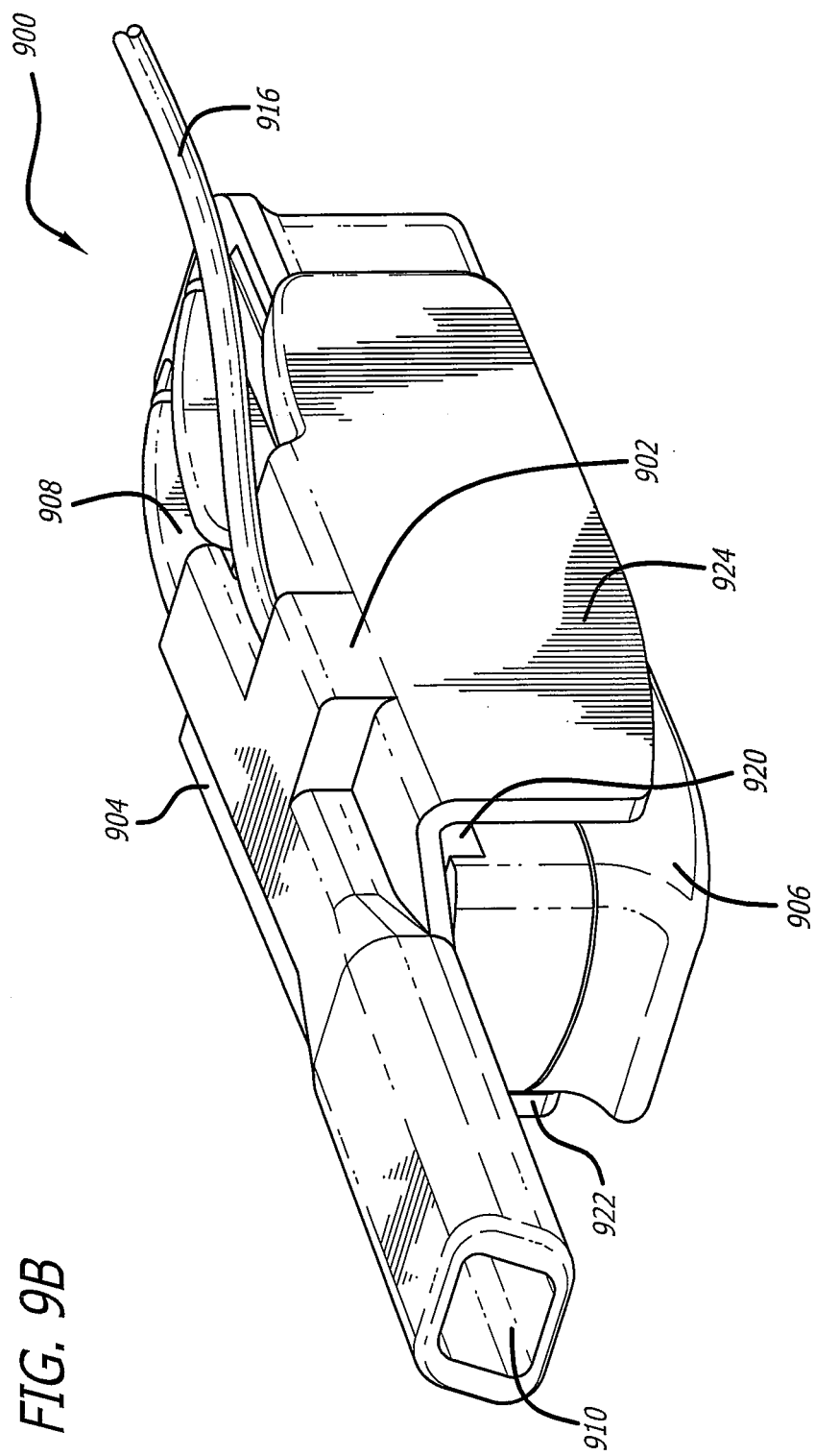
Figure 10:
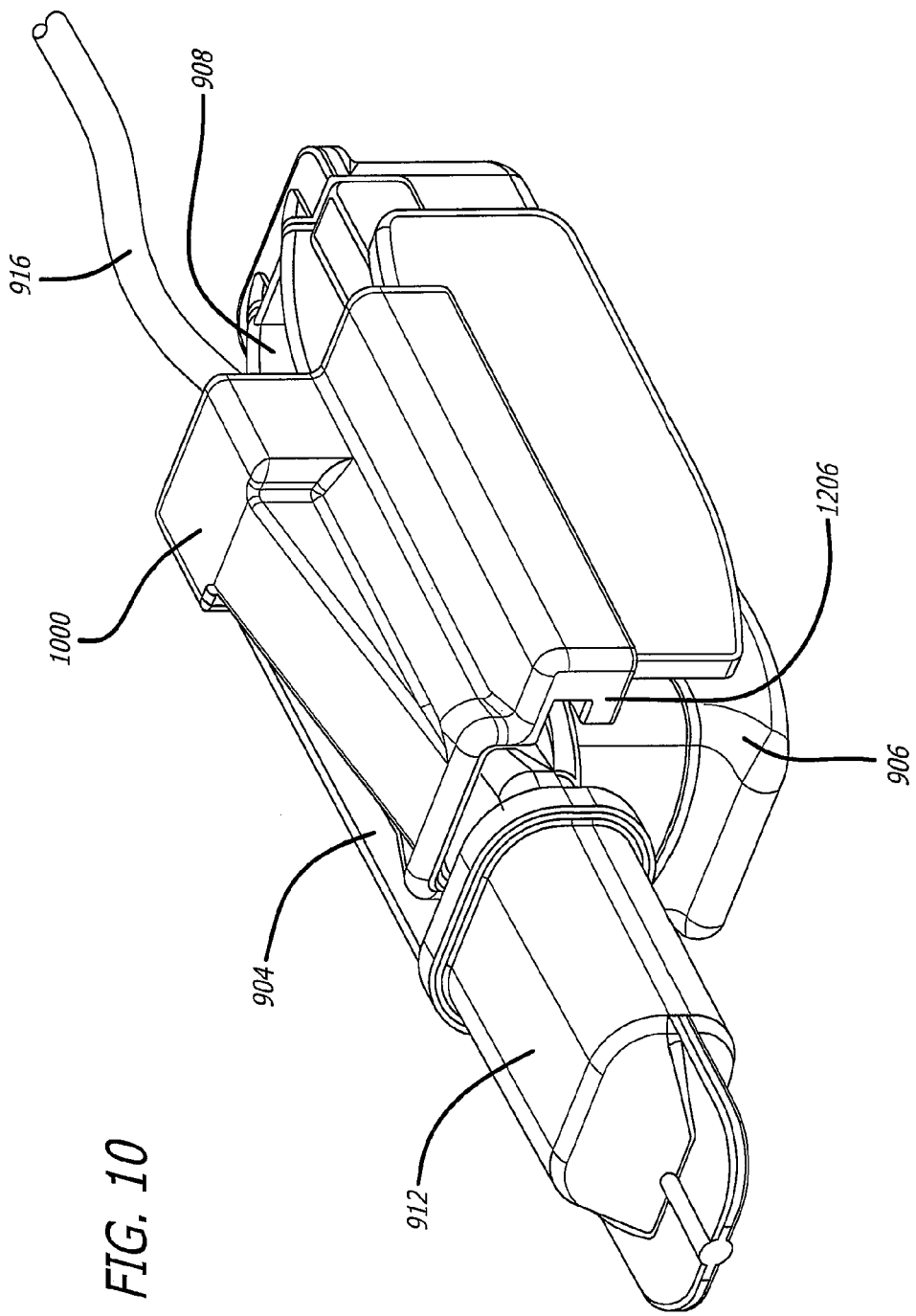
FIG. 10 illustrates an isometric view of yet an alternate embodiment of a sensing and/or monitoring device provided as part of a jacket adapted to a dry powder inhaler.

In another exemplary embodiment illustrated in FIGS. 9A and B, dry powder inhaler 900 can be provided with a sensing and/or monitoring device 902 which can monitor and/or sense signals generated by or within dry powder inhaler 900 during an inhalation maneuver by a patient. FIG. 9A illustrates dry powder inhaler 900 without a sensor device either integrated into the device or attached thereto. Alternatively, in an exemplary embodiment depicted in FIG. 9B, monitoring device 902 can be provided as an integral part of dry powder inhaler 900 on mouthpiece 904 or housing 906 as desired. Dry powder inhaler 900, as depicted in FIG. 9B, has monitoring device 902 adapted within the inhaler, which comprises mouthpiece 904 and housing 906. In one embodiment, the sensor can be integrated within the component walls of inhaler 900, including the mouthpiece, housing, or sled to project into one of the flow pathways of the inhaler. Dry powder inhaler 900 comprises an air conduit with an air inlet 908, air outlet 910 and optional mouthpiece cover 912 (FIG. 10). Monitoring device 902 including a small or miniature microphone is provided within dry powder inhaler 900 configured with mouthpiece 904 and is provided with leads 914 (FIG. 13), which can be connected to an analog to digital converter, a display device, and/or a computer.

Figure 11:
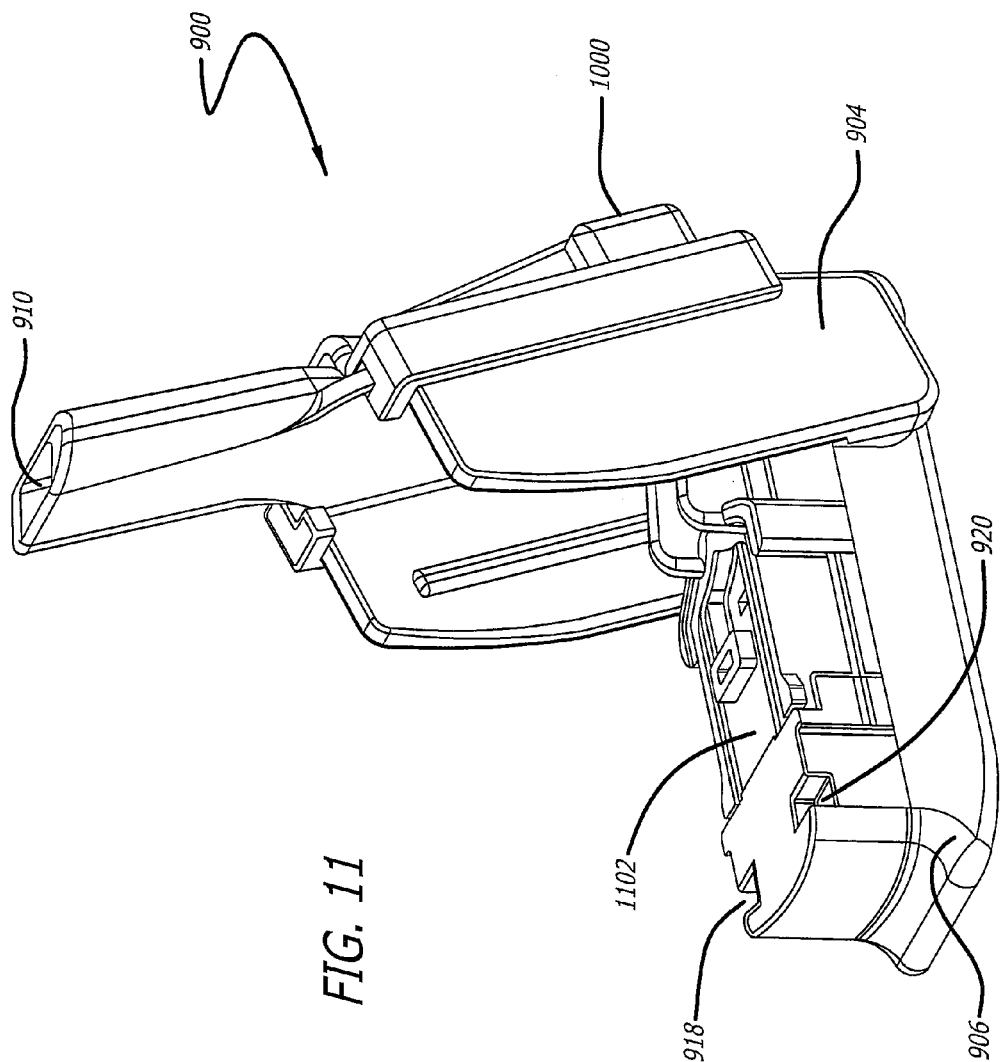
FIG. 11 illustrates an isometric view of the sensing and/or monitoring device illustrated in FIG. 10, wherein a dry powder inhaler system is depicted in an open configuration.
Figure 12:
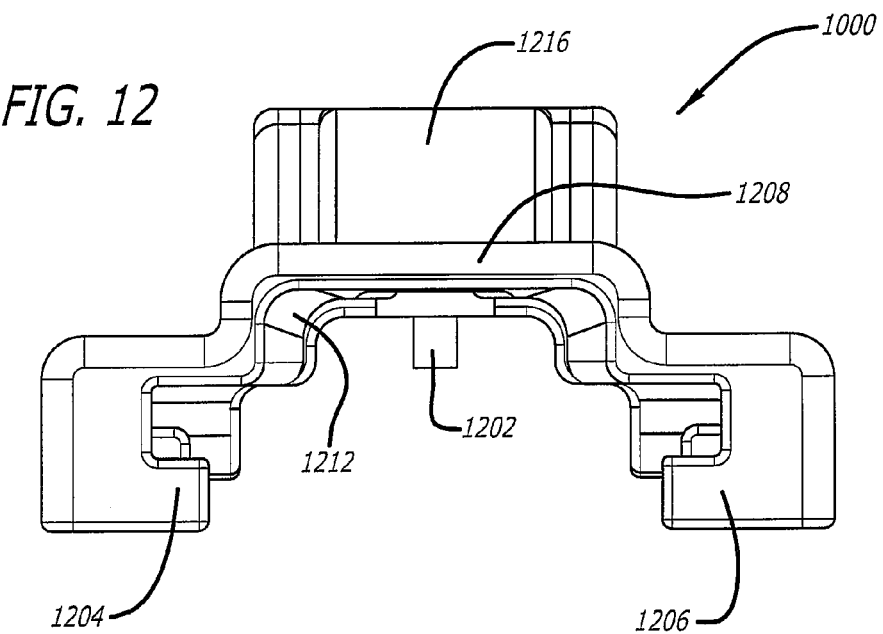
FIG. 12 illustrates a back view of the sensing and/or monitor device shown mounted onto a dry powder inhaler as shown in FIGS. 10 and 11.

FIGS. 10-16 depict alternate embodiments, wherein dry powder inhaler 900 includes detachable sensing and monitoring device 1000 presented as a jacket or cap, wherein detachable sensing and monitoring device 1000 can be provided as a detachable part that can adapt to a dry powder inhaler. In this embodiment, the jacket is manufactured as a separate, detachable device comprising sensors, for example, a microphone which can detect signals and being capable of storing, transmitting or displaying the signals. In one embodiment, the sensor is placed in the bottom portion of the jacket as depicted in FIG. 12 so that the sensor is placed in an air conduit of the inhaler. In other example embodiments, a wireless device can also be provided in connection with the sensor. Sound waves emanating from the inhaler in use with or without a dry powder are detected by the microphone and the signals can be analyzed and correlated to time of powder discharge in the presence of a dry powder, airflow rate, end of powder discharge during an inhalation maneuver, temperature within the inhaler pathway, and the like, depending on the type of sensor used. For example, an increase in sound can be correlated to an increase in flow rate through the device, and/or powder particles collisions in the air stream during delivery.

A sensor such as a microphone, as a result of its small size, can be placed anywhere in the inhaler. In embodiments wherein the sensor is a pressure transducer, the sensor can be placed within an air conduit passing through one of the inhaler compartments. The sensors can be provided, for example, in an air conduit on or within the inhaler or provided as a separate, detachable part as an accessory to the inhaler with a shape or configuration that can be adapted to the inhaler to which it is to be adapted, and can include a cap, a jacket, sleeve or a saddle-like configuration that can be adapted or mounted to the inhaler. For the detachable embodiments, the sensing and monitoring apparatus is easy and inexpensive to manufacture and can be made from plastics, and works well with high resistance dry powder inhalers. In the embodiment illustrated in FIG. 10, for example, sensor 1202, depicted in FIG. 12, is provided within the air conduit of mouthpiece 904. The sensor can be any sensor, for example, a thermocouple wire, a pressure transducer, an analog sensor, a microphone, an optical sensor, a gas sensor, or any sensor that can detect signals generated within an inhaler. Sensor 1202, for example is a microphone. The sensors described herein can be adapted to communicate or transmit signals with a wireless device or the signals can be transmitted or stored using wire connection 916 to an analog to digital converter.

Alternatively, an analog to digital converter is provided within the inhaler device and resulting digital data is transferred out of the device directly. The signals provided by the sensors described herein can be in the form of sound generated in an inhaler by airflow passing through the air conduits and/or powder particles collisions entrained in the air flow pathway. Signals generated from the inhaler can be detected by the sensors and stored, transmitted or displayed. Data can be generated from the signals and qualitatively and/or quantitatively analyzed. In this manner, measurements can be made including time of dose release.

FIG. 11 depicts an isometric view of the sensing and/or monitoring device illustrated in FIG. 10, wherein dry powder inhaler 900 is depicted in an open configuration. Dry powder inhaler 900 comprises mouthpiece 904, housing 906, and a hinge mechanism, including a gear, for opening and closing dry powder inhaler 900. Movement of mouthpiece 904 to an open configuration as shown in FIG. 11 permits mounting of cartridge 1102 for dosing. Movement of mouthpiece 904 onto housing 906 into a closed or dosing position, as illustrated in FIG. 9, of dry powder inhaler 900 which comprises a slide tray attached to the hinge mechanism, reconfigures cartridge 1102 to a dosing position forming an air pathway through cartridge 1102 and mouthpiece 904.

In one example embodiment, detachable sensing and monitoring device 1000 (FIGS. 12, 13, and 16) can be used as needed by a patient or a health provider in training or gathering information from the patient's inhalation maneuvers and then removed from dry powder inhaler 900, at which point dry powder inhaler 900 remains functional. FIG. 11 depicts an example embodiment wherein detachable sensing and monitoring device 1000 is adapted to mouthpiece 904 so that it fits securely and cannot move during loading or unloading cartridge 1102 with repeated use. Detachable sensing and monitoring device 1000 can be removed after use and remounted onto another inhaler as needed. In this embodiment, the detachable system provides a simple device that does not interfere with, or affect with the characteristic resistance values of the inhalation system.

FIG. 12 illustrates a back view of detachable sensing and monitoring device 1000 shown mounted onto dry powder inhaler 900 in FIGS. 10 and 11, removed from an inhaler. As illustrated in FIG. 12, detachable sensing and monitoring device 1000 is configured to have first flange 1204 and second flange 1206 both of which can engage mouthpiece 904 so that a secure fit can be obtained and can clear housing 906 by sitting within corresponding first groove 918 and second groove 920 on dry powder inhaler 900 when in a closed position. In such an example embodiment, dry powder inhaler 900 can comprise wire connection 916 or at least one lead which can couple to an analog to digital converter so that signals detected by sensor 1202 on traversing portion 1208 of detachable sensing and monitoring device 1000 can be transformed into data. In an alternate example embodiment, detachable sensing and monitoring device 1000 can be adapted to a wireless transmitter to send measured signals to a receiver.

Figure 13:
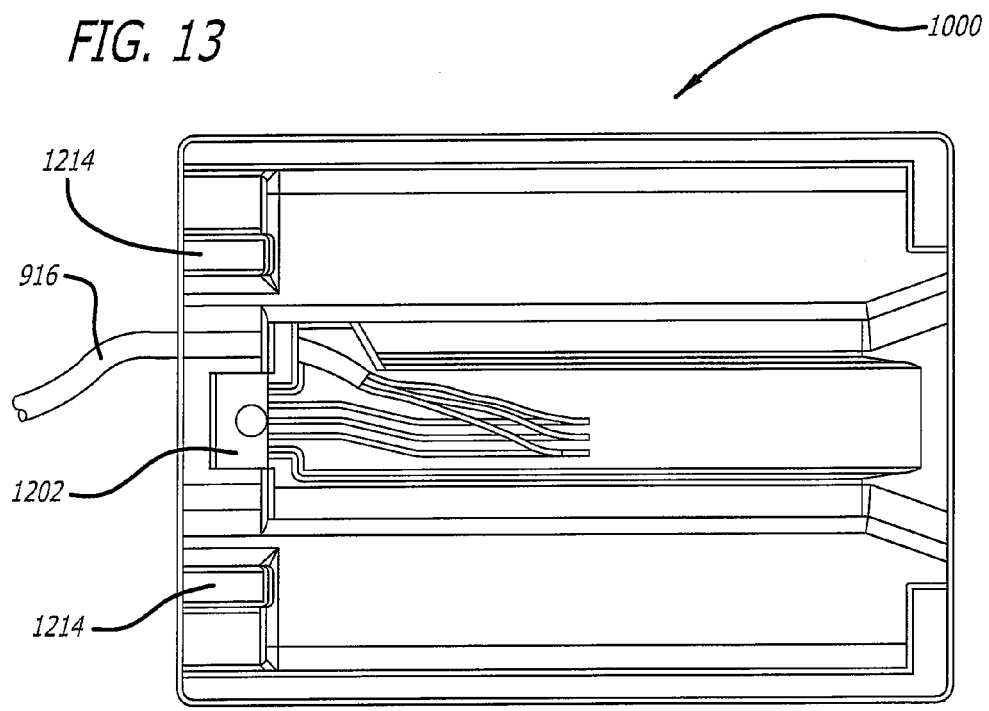
FIG. 13 illustrates a bottom view of the sensing and/or monitor device illustrated in FIG. 12.
Figure 16:
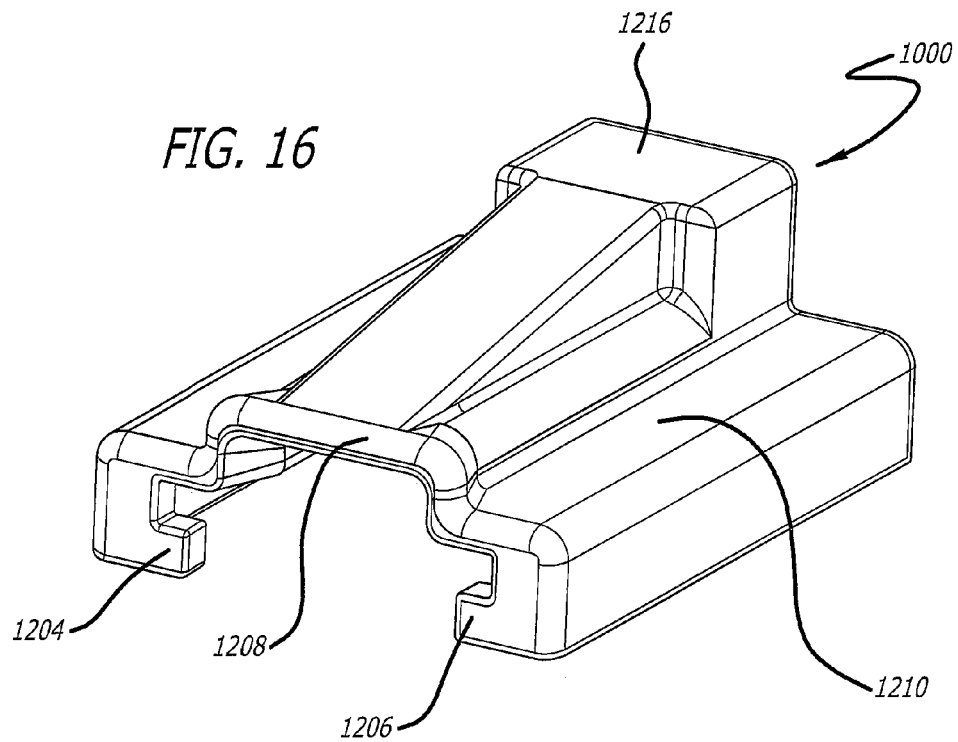
FIG. 16 illustrates an isometric view of the embodiment of the sensing and/or monitoring device depicted in FIGS. 10-15.

FIGS. 12 and 16 illustrate detachable sensing and monitoring device 1000 configured in the shape of a saddle to correspond to different dry powder inhaler configurations. Detachable sensing and monitoring device 1000 has top surface 1210, bottom surface 1212 and sensor 1202 configured on bottom surface 1212 of detachable sensing and monitoring device 1000 in a mid-longitudinal axis. Detachable sensing and monitoring device 1000 can also comprise at least one detent or at least one protrusion 1214 in addition to first flange 1204 and second flange 1206 to engage and adapt to dry powder inhaler 900. In one example embodiment, detachable sensing and monitoring device 1000 comprises a raised area 1216 with a hollow undersurface configured to hold sensor wires 1302 so as to avoid any obstruction of airflow in the air conduit of dry powder inhaler 900. FIG. 13 depicts a bottom view of detachable sensing and monitoring device 1000 illustrating sensor 1202 coupled to sensor wires 1302 and wire connection 916 for connecting to a digital to analogue converter.

Figure 14:
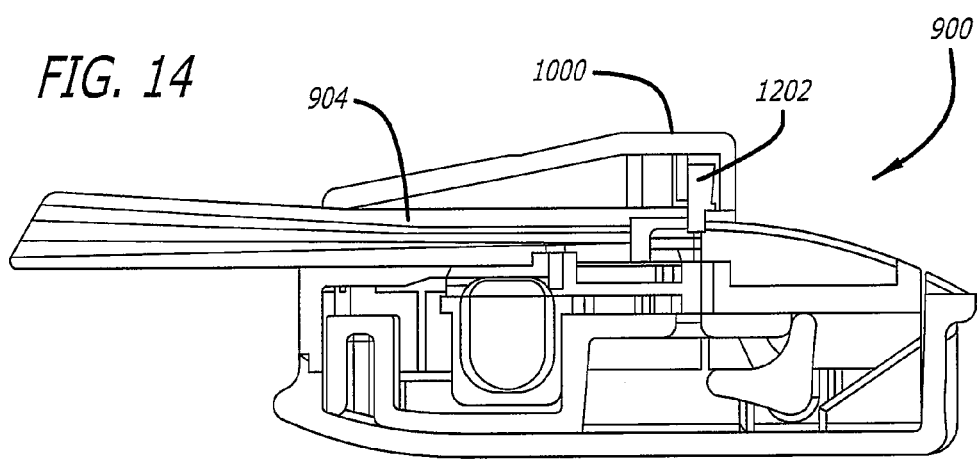
FIG. 14 illustrates a side view of a dry powder inhaler in cross-section through its mid-longitudinal line with a cartridge in place and equipped with a sensing and/or monitoring device.
Figure 15:
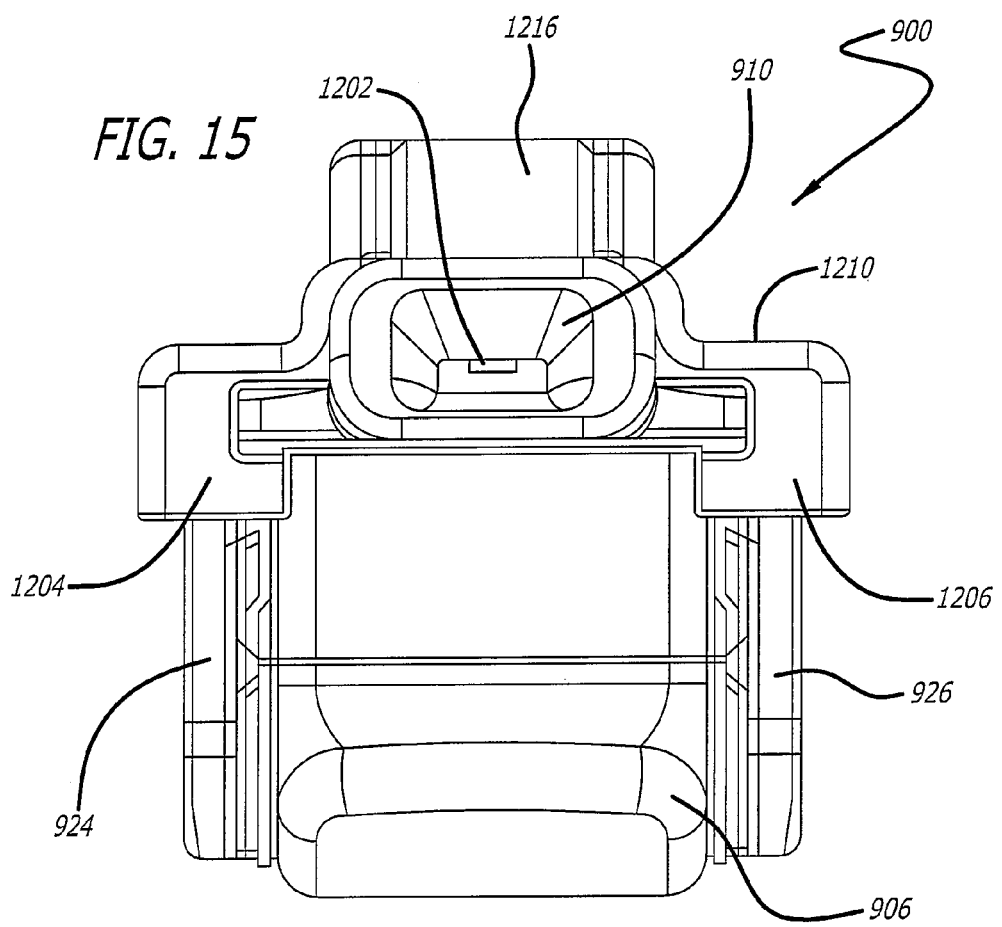
FIG. 15 illustrates a proximal view of a dry powder inhaler equipped with a sensing and/or monitoring device.

FIG. 14 illustrates a cross-sectional side view of dry powder inhaler 900 equipped with detachable sensing and monitoring device 1000 shown in FIG. 11. The cross-section is through its mid-longitudinal line with cartridge 1102 in place and showing the position of sensor 1202 within the jacket. FIGS. 14 and 15 also show the position of sensor 1202, for example a microphone, in the air pathway of mouthpiece 904. In some embodiments, the sensor within the jacket for adapting to an inhaler's air pathways can be configured in different places depending on the inhaler. In this manner, the jacket can be configured to have the sensor integrated so when adapted to the inhaler it is positioned upstream, downstream or in the middle of the inhaler's air conduit so that the sound signals or vibrations can be detected through the wall of the inhaler or directly on the air pathway.

Figure 17:
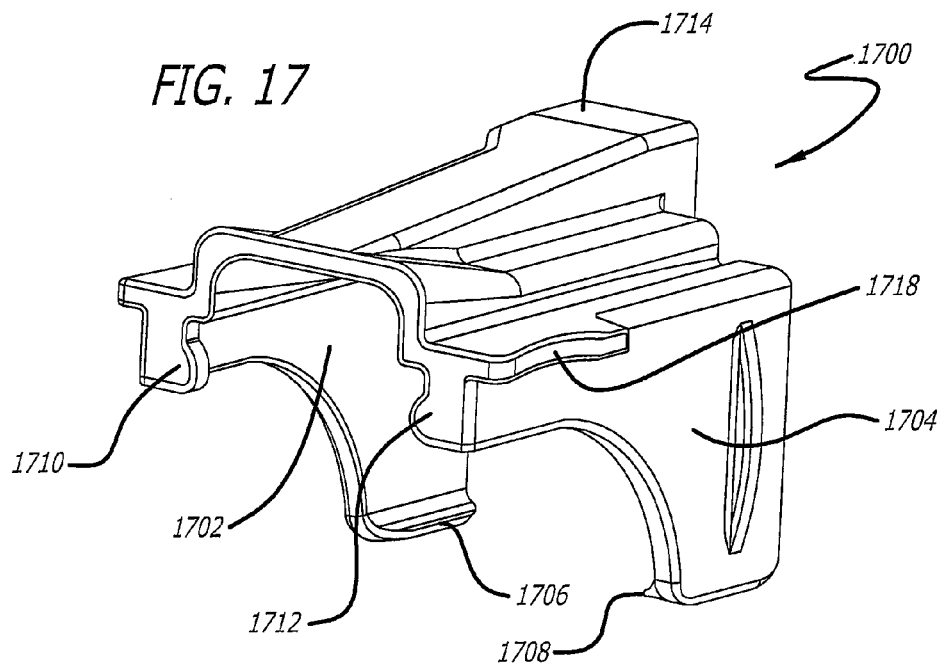
FIG. 17 illustrates an isometric view of an alternate embodiment of a sensing and/or monitoring device for adapting to a dry powder inhaler.

FIG. 17 depicts an isometric view of alternate detachable monitoring device 1700 configured to be adapted to a dry powder inhaler such as dry powder inhaler 900. In this example embodiment, first side panel 1702 and second side panel 1704 can adapt to first inhaler side panel 922 and second inhaler side panel 924 of mouthpiece 904 to form a tight fit with dry powder inhaler 900. Alternate detachable monitoring device 1700 further comprises first bottom flange 1706, second bottom flange 1708, first front flange 1710 and second front flange 1712 used to engage with dry powder inhaler 900. First bottom flange 1706 and second bottom flange 1708 grasp the bottoms of first inhaler side panel 922 and second inhaler side panel 924 while first front flange 1710 and second front flange 1712 grasp the sides of mouthpiece 904 and fit within first groove 918 and second groove 920 on dry powder inhaler 900. Alternate detachable monitoring device 1700 further includes raised area 1714 for housing a sensor and accompanying wires (not illustrated) in its undersurface. Grasping area 1718 facilitates handling of the jacket.

Figure 18:
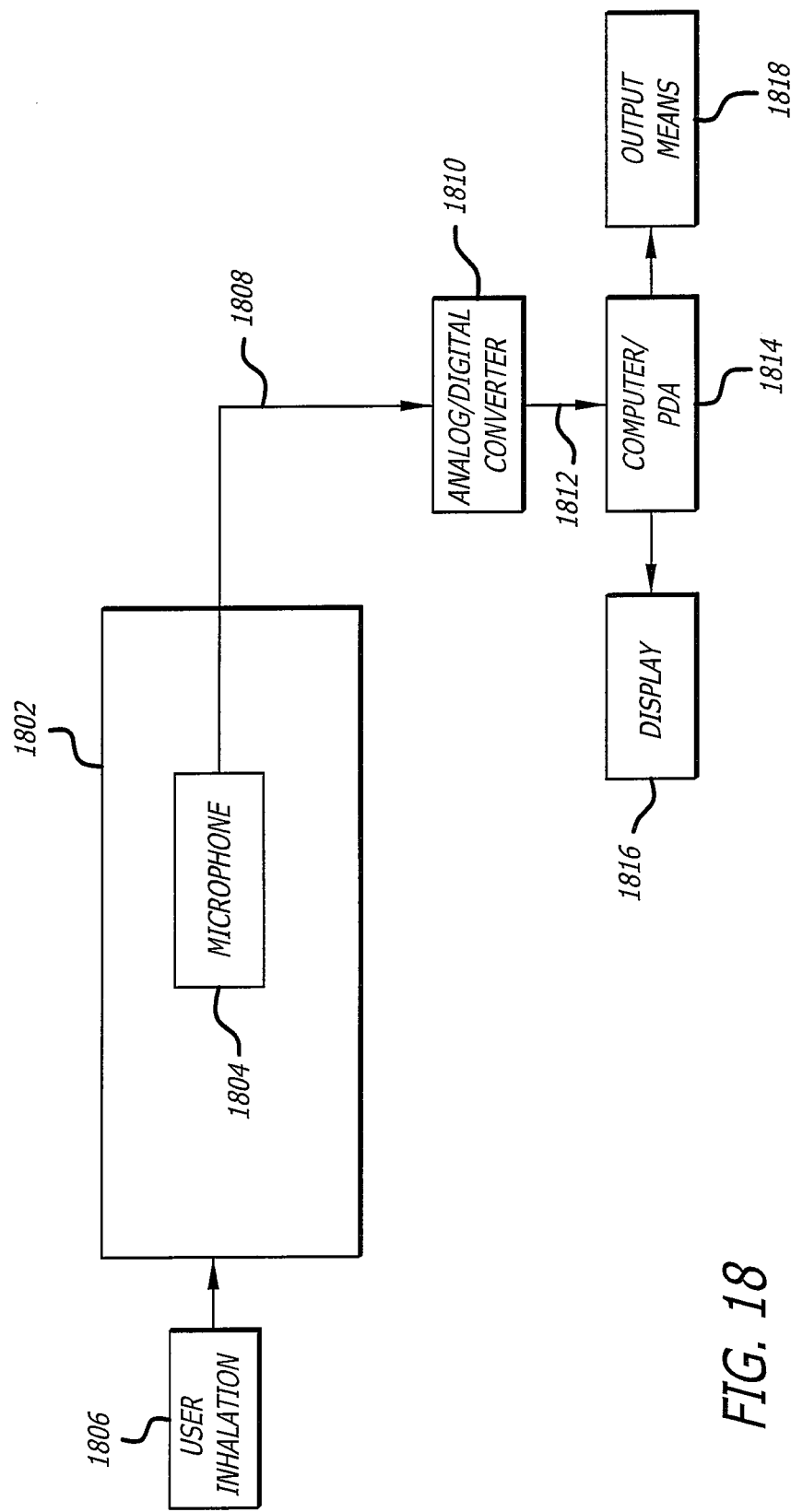
FIG. 18 illustrates a block diagram of the overall exemplary sensing and/or monitoring system disclosed herein.

FIG. 18 illustrates block diagram 1800 for an exemplary configuration of an overall sensing and/or monitoring device and system as disclosed herein. In such an example embodiment, inhaler 1802 comprises microphone 1804 to detect user inhalation 1806 and provide analog signal 1808. During user inhalation 1806, sound waves generated by the airflow as it enters the air conduits of inhaler 1802 are detected by microphone 1804. Microphone 1804 can detect sound signals generated from alteration in pressure, stress, particle displacement and particle velocity of an inhaler in use, the range from 15 to 20,000 Hertz. Microphone 1804 uses the signal pattern resulting from the changing or variations in frequency emissions intrinsically being generated from the inhaler in use with and without powder to determine the flow rate or pressure within the device that when analyzed can be correlated to user and/or device performance. These vibratory signals in microphone 1804 are then converted into analog signal 1808

(e.g. voltage) and transmitted to analog to digital converter 1810. Signals from the analog/digital converter 1812 are communicated to computer/PDA 1814 provided with a microprocessor which uses an algorithm for analyzing the signals received from the analog/digital converter 1812. The processed data is presented with frequency, time and amplitude parameters, and provided on display 1816 or provided to an output means 1818 for storage for future use, communication to a web based digital storage, and/or printing out. In such an example embodiment, by monitoring the signal frequency versus time, the amplitude of analog signal 1808 can be determined. Each dry powder inhaler type can have a typical acoustical pattern, or fingerprint, which develops for the inhaler in use, and the pattern can then be detected and converted to specific signals, analyzed and stored or displayed in a display device such as a computer monitor.

In another embodiment, a sensing and monitoring system for an inhaler includes a sensing and/or monitoring device structurally configured to be adapted to an inhaler; an analog to digital converter; and a data storage medium. The data storage medium includes a disc drive, a CD-ROM, a server, a flash card or drive, memory card, and the like and includes a set of machine-readable instructions that are executable by a microprocessor or other processing device to implement an algorithm. The algorithm, when run, initiates the steps of generating a logical sub-system generation number derived from detected signals; saving the logical sub-system generation number to a data track within a logical sub-system, wherein the logical sub-system generation number and a cluster generation number in the processing device are compared; and storing and/or displaying information from the algorithm as the results from an inhalation maneuver.

Figure 19:
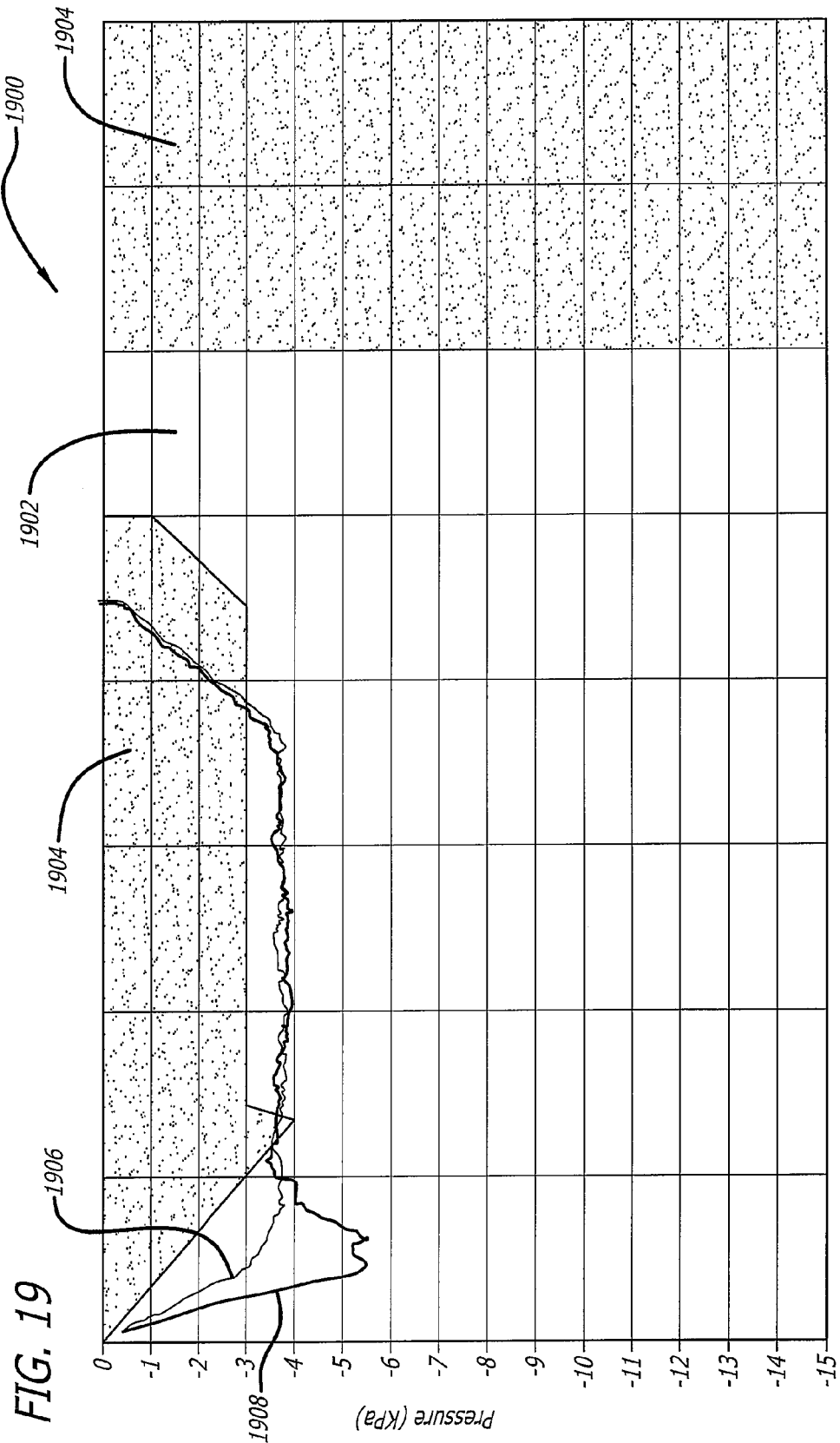
FIG. 19 graphically illustrates an inhalation maneuver performed by a subject trained to take a deep breath and illustrating profiles with and without a dry powder dose tested at the same pressure differential.

FIG. 19 illustrates an exemplary graphic display 1900 of an inhalation maneuver performed using a dry powder inhaler system in response to a pressure differential, wherein the dry powder inhaler system comprised a microphone sensor. Similar to FIGS. 6-9, graphic display 1900 has acceptable region 1902 and unacceptable region 1904. These regions can be colored red and green or any other combination of colors that aid in learning the inhalation maneuver. The subject is coached to take a deep breath with the inhaler for about a period of 4 to 5 seconds and allowed to exhale normally. The graph illustrates inspiratory profiles from the subject showing measurements using a sensing and monitor device described in FIGS. 10-16. FIG. 19 illustrates the data as time in the x-axis and pressure differential in the y-axis.

The inhalation maneuvers were performed using the inhaler with a cartridge without a dry powder formulation, depicted by first curve 1906, and with a dry powder formulation, depicted by second curve 1908. The results show that the sensing and monitoring device can detect the presence of powder emitted from the system, the time of powder emission and the amount of powder emitted from the system. Curve 1906 is the signal produced by the microphone during an inhalation without powder in the system and curve 1908 is the signal produced by the microphone during the same inhalation with powder in the system. The difference of the curves 1908 and 1906 represents the presence and magnitude of powder emitted from the system and time of emission. The data in FIG. 19 illustrate that the sensing and monitoring device is effective for measuring the amount of dose emitted from the inhaler cartridge system.

In one exemplary embodiment, each component of the inhalation simulation system can be used independent of the other. In one embodiment, the second component of the inhalation simulation system can be used alone or with stored information from an inhalation profile performed by a patient and stored in the computer analyzed with algorithm and programmed software in the computer which can replicate the patient's inhalation effort in vitro using several additional devices. The inhalation simulation system can comprise individual patient profiles and the system can be programmed with specific parameters simulating or replicating the patient inhalations, which can be used, for example, to test the inhaler performance given for use, design and develop inhalers for the individual's need at specific inhalation efforts, and determine the powder performance of the inhaler.

Figure 20:
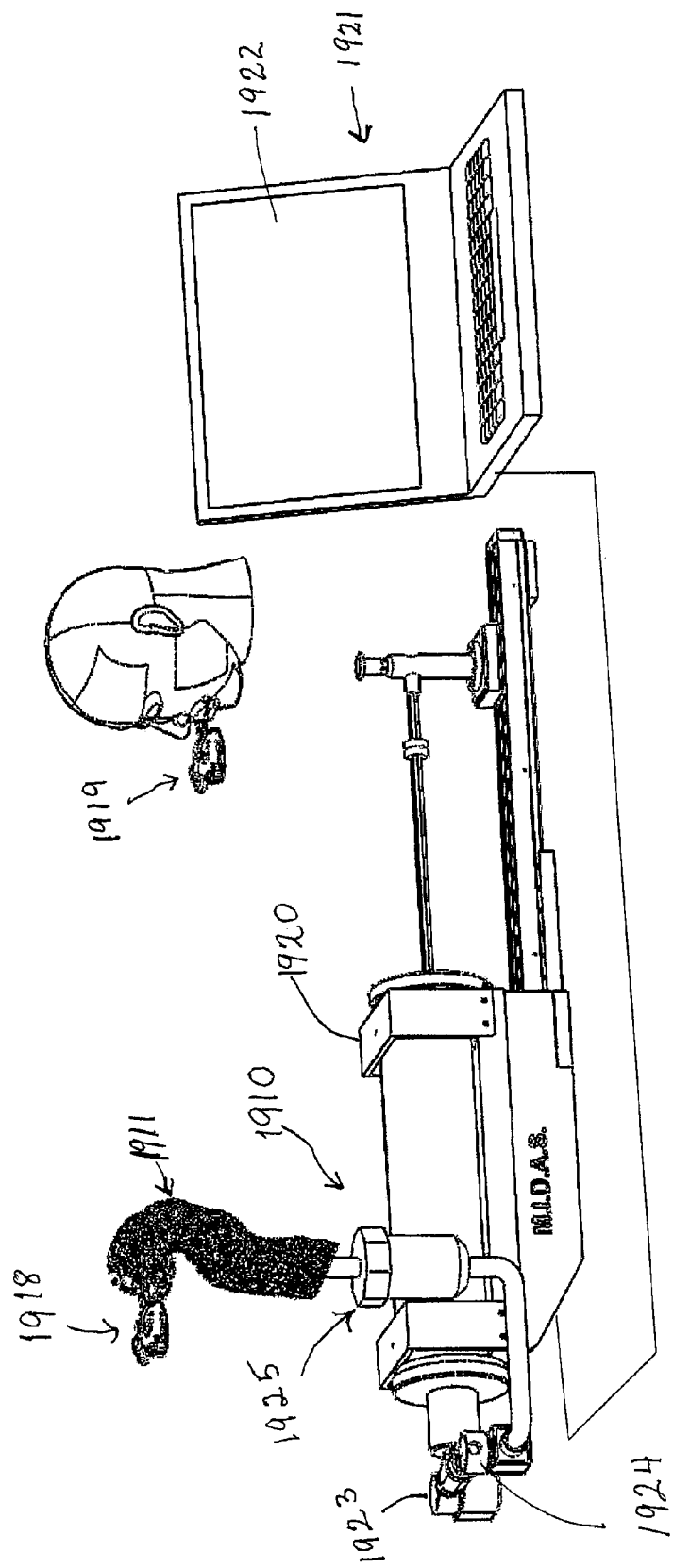
FIG. 20 graphically illustrates an alternate embodiment of a dry powder inhaler training or monitoring and sensing apparatus used in combination with a system for reproducing or simulating a patient's inhalation maneuver.
Figure 21:
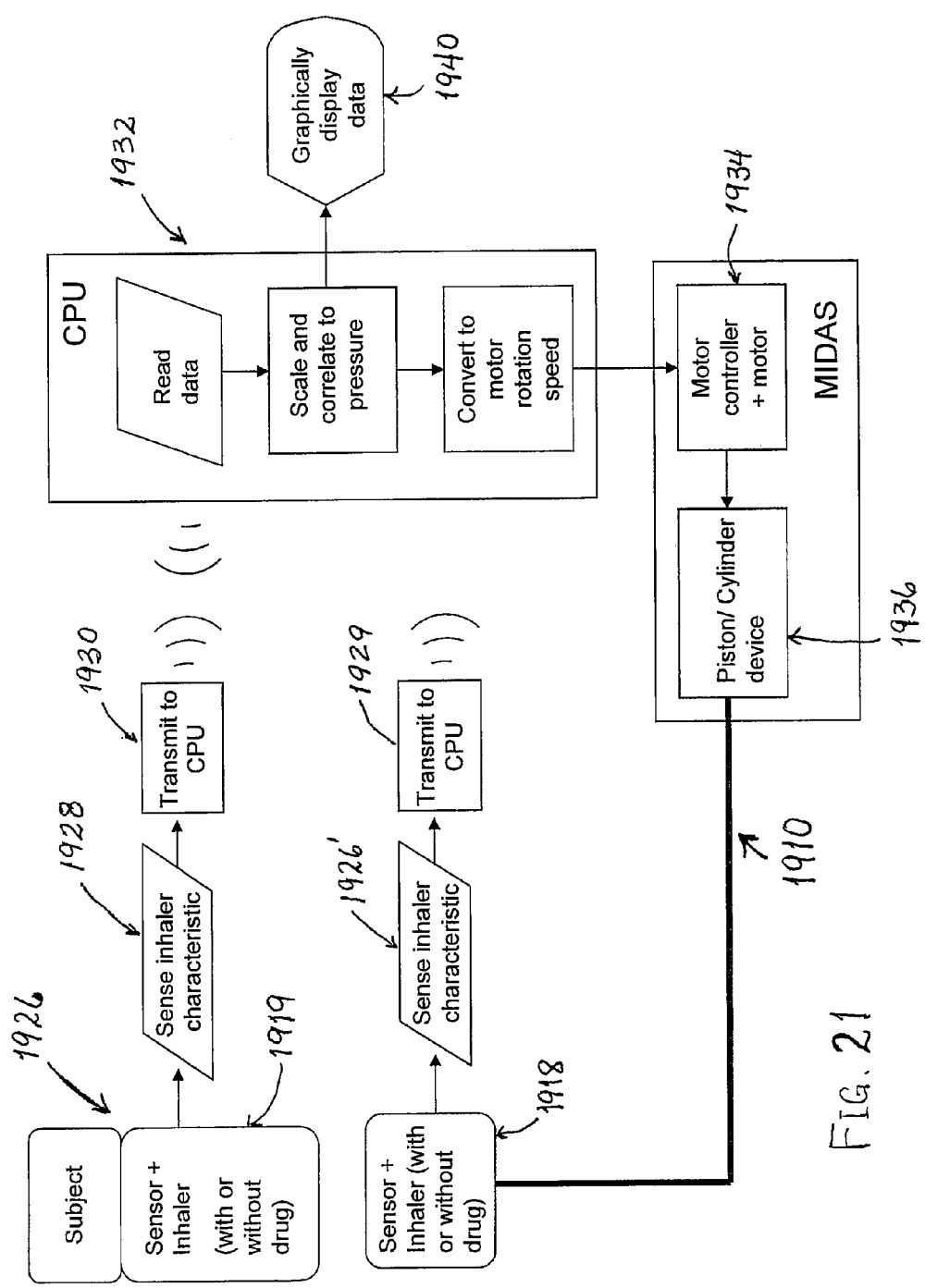
FIG. 21 illustrates a block diagram of the overall exemplary sensing and/or monitoring device combined with the inhalation simulator system disclosed herein.

In an exemplary embodiment, the inhalation simulation system 1910 is illustrated in FIG. 20 and FIG. 21. FIG. 20 is a graphic illustration of an embodiment of the inhalation simulation system showing aspects of the first and second components. Inhalation simulation system 1910 comprises a first inhalation apparatus 1919 comprising a dry powder inhaler with an attachable sensing and monitoring system which is part of the first component. The second component of system 1910 comprises an identical inhalation apparatus 1918, which reproduces a patient's inspiratory profile data stored or acquired simultaneously by computer 1921.

FIG. 20 depicts a dry powder inhaler training or monitoring and sensing apparatus 1918 used in combination with a system for reproducing or simulating a patient's inhalation maneuver of the first apparatus 1919. Data obtained from the inhalation maneuver by the sensing and monitoring system 1919 is transmitted to a receiver wherein the simulation system can store or reproduce the inhalation parameters generated by the patient either simultaneously or at a later time. In this embodiment and as illustrated in FIG. 20, the simulation module system 1910 comprises a sensing and monitoring device 1918, which comprises: a housing, a battery (not shown), a sensor and a radio transmitter, which as shown, is a wireless jacket adapted to an inhaler. The monitoring and sensing device 1919 as used by a patient can sense at least one aspect of an inhalation device's performance, for example, flow, pressure differential, and/or sound, during an inhalation. Signals detected can be converted into data signals and transmitted by a wired or wireless transmitter to a computer 1921 comprising a receiver and microprocessor implementing an algorithm for controlling the simulation system 1910. In particular embodiments the data can be displayed in real-time, for example on a monitor 1922. The data that is relayed to a computer comprising the algorithm can be displayed in real time, or stored for use in simulation runs at a later time or for further analysis.

In one embodiment, the inhalation simulation system 1910 comprises an artificial, substantially accurate anatomical head 1911 comprising a model of the upper respiratory tract/airway, the benhead, which is substantially accurate and a representative model of a male upper airway, bisected into two halves in the longitudinal axis through the center, which halves make a tight seal in use. The benhead can be made from an epoxy resin having a mouth and an opening in the opposing end which can be adapted to various devices, for example, a filtration system, artificial lungs, flow meter, and to the a vacuum source, such as a calibrated syringe pump. The inhalation simulation system also comprises a monitoring and sensing device 1918 which can be an integral part of an inhaler or coupled to an inhaler, a power source (not shown), a motor controller, a motor, a piston/cylinder assembly 1920 which works as a syringe pump, a computer comprising a microprocessor 1921 with an algorithm and in particular embodiments a display monitor 1922 for visualizing output data gather by the simulation system. The simulation system can also comprise a filter adaptor and sample tube 1925 and filter such as glassfiber filters provided by Pall Life Sciences, for preventing powder from entering the simulation system 1910 other components, valves 1023, 1924 for controlling flow. Powder can be recovered from the filter and sample tube for quantitation of a dose delivery and quality of dose.

In operation, the motor controller receives motion specific input from a computer based on the information stored or simultaneously received in the system. Once the controller is activated to control the motion of an electrical motor, which is mechanically coupled to a piston such that rotational motion of the motor is translated into linear motion of the piston. As the piston moves, the volume in the cylinder changes thereby creating flow into the cylinder which creates a vacuum in the conduits of inhaler device adapted with monitoring and sensing device 1918. Sound generated as a result of the pressure differential/airflow generated in inhaler 1918 is then captured by the sensor in the device or attached to the device. In an alternate embodiment, the sensor can be integrated within the dry powder inhaler. If a powder formulation is contained in inhaler with sensor 1918, the pressure drop generated in the device can cause the powder to be emitted from the inhaler and flow, pressure differential and/or sound can be detected by the sensing and monitoring device 1918 and transmitted to the computer 1921.

In one embodiment, sensing and monitoring device 1919 is coupled with inhalation simulation system 1910 to provide an apparatus that can be configured to measure flow in a patient's inhaler in use, without dose, and which can reproduce the same flow characteristics, for example, rate, magnitude, duration of an inhalation maneuver in a second device, with dose. In this embodiment, a patient can inhale without exposure to an active drug, and inhaler and patient's performance measurements can be ascertained, including, for example, amount of dose emitted from an inhaler, particle size distribution, and the like can be made on the resulting discharge. In alternative embodiments, 1918 can comprise only an inhaler from which the dose can be delivered to the simulator system, or it can further comprise monitoring and sensing means so that the fidelity of the simulation of the patient's inhalation maneuver can be assessed. In some embodiments, the filter adaptor 1925 further comprises a transparent tube (not shown) to allow visual observation of the "inhaled" bolus of powder, for example by eye or by high speed video camera. In alternate embodiments, a laser diffraction device can be used to measure the plume emitted from the dry powder inhaler containing the powder composition. The laser diffraction system can be adapted to measure the particle size distribution of the plume as it crosses by the transparent tube.

FIG. 21 illustrates a block diagram of the overall exemplary embodiment of the inhalation simulation system 1910 components interact with one another. In operation, an inhaler 1926, such as a dry powder inhaler, can be coupled with a removable monitoring and sensing device 1919, such that the monitoring and sensing device 1919 is positioned on the inhaler near a position of moving flow. Upon inhalation, flow is generated through the device 1926 and sensed by a sensor within the sensing and monitoring apparatus 1919. In one embodiment, the sensor can comprise a microphone, which can be used to measure the sound generated by the flow moving through the conduits of the inhaler 1926. Experiments have shown that the amplitude of the sound correlates well with the magnitude of the pressure drop across the inhaler 1926. In other embodiments, the sensor can comprise a pressure transducer or a flow meter. The sensed flow is converted to an electrical signal which is characteristic of the inhaler 1928 by the sensor and relayed to a radio device 1930 operating, for example, wireless protocols such as Bluetooth or Zigbee, within the housing. The radio device 1930 then transmits the data to a computer or microprocessor 1932 for analysis, display 1940 and/or storage. As the data is received by the computer 1930, the data signals are scaled and correlated to pressure, and ultimately converted to a rotational speed used by the motor controller to drive the motor 1934 so that the information received is reproduced by the simulation system 1910 to generate a pressure differential in the piston/cylinder device 1936 creating a flow in inhaler-monitoring and sensing system 1918. Sound signals generated from the inhaler adapted to the Benhead in the simulation system are detected from the flow by the sensing and monitoring device 1918, which sound signals are characteristic of the inhaler 1926' and converted to electrical signal by the sensor and relayed to a radio device 1929 operating, for example, wireless protocols such as Bluetooth or Zigbee, within the housing. The radio device 1929 then transmits the data to the computer or microprocessor 1932 for analysis, display 1940 and/or storage.

In one embodiment, the inhalation simulation system 1910 is configured to be unidirectional so that the flow is in one direction. Valves 1923 and 1924 are provided to allow the system to return to the start position after use. In one embodiment, the respiratory tract of an anatomical artificial head 1911 can be used with or without artificial mucous to mimic in vivo affects of powder deposition during dose delivery. In an embodiment, the inhalation simulation system can comprise a camera for recording the quality of a plume emitted from a powder contained in the inhalation device 1918 during use.

Example 1

Using an Integrated Training Device

A 57 year old Type II diabetic is instructed to receive inhaled insulin from a dry powder inhalation system, because she has an elevated hemoglobin A1c and is considered out of control. The patient is trained for inhalation using a device as illustrated in FIG. 9B with an integrated sensor. The patient is given the device and asked to take a deep rapid breath in using the training device.

The data is collected on a computer and the patient is able to view the data in real-time on a display screen. The patient's first inhalation attempt is too slow and is indicated on-screen as entering a red "unacceptable region." The patient is instructed to take another rapid breath in that is slightly faster than the previous attempt. Upon completion of the inhalation, the graph illustrates that the patient's inhalation maneuver was acceptable and entirely in the green region of the graph. Upon being comfortable with the training, the patient is clear for use of a similar device.

The patient is prescribed a dry powder inhaler similar to the type that illustrated in FIG. 9A and cartridges filled with an inhalable insulin for treatment of the patient's diabetes. Six months after prescribing the inhaled insulin, the patient's diabetes is diagnosed as under control.

Example 2

Using an Attachable Training Device

A 59 year old Type II diabetic is instructed to receive inhaled insulin from a dry powder inhalation system. The patient has requested the inhalation system for convenience reasons. The patient is trained for inhalation using a device as illustrated in FIG. 9A. The patient is given the device fitted with an attachable sensor similar to that if FIG. 12 and asked to take a deep rapid breath in using the training device.

The data is collected on a computer and the patient is able to view the data in real-time on a display screen. The patient's first attempt is acceptable as indicated by the software. Upon being comfortable with the training, the patient is clear for use of the device.

The patient attachable sensor is removed from the dry powder inhaler. The patient is given the dry powder inhaler and cartridges filled with inhalable insulin for treatment of the patient's diabetes. Six months after prescribing the inhaled insulin, the patient's diabetes is diagnosed as under control and the patient comments on the great convenience of the device.

Example 3

Using an Attachable Training Device and a Dry Powder Inhaler to Assess Inhaler Performance with an Inhalation Simulation System A 45 year old Type II diabetic is instructed to receive inhaled insulin from a dry powder inhalation system. The patient has requested the inhalation system for convenience reasons. The patient is trained for proper inhalation maneuvers using a device illustrated in FIG. 9A. The patient is given the device fitted with an attachable, wireless sensor device configured in a jacket attachable to the inhaler similar to that illustrated in FIG. 12. The patient is asked to inhale deeply while using the inhaler with the training device until the patient attains his preferred inhalation profile when compared to a standard profile provided with the system and displayed in a monitor while performing the inhalation.

Once the patient feels comfortable attaining his preferred inhalation profile, the patient is asked to inhale in proximity to an actuated simulation inhalation apparatus as described above. The patient's training device system can communicate with a computer to actuate the simulation system. The simulation inhalation apparatus is adapted with an inhaler of the same type as the one use by the patient, which inhaler is adapted with its own attachable wireless sensor device as that of the patient's inhaler, and containing a dry powder formulation comprising insulin and fumaryl diketopiperazine(bis-3,6-(N-fumaryl-4-aminobutyl)-2,5-diketo-diketopiperazine; FDKP) of the prescribed dose ordered.

Figure 22:
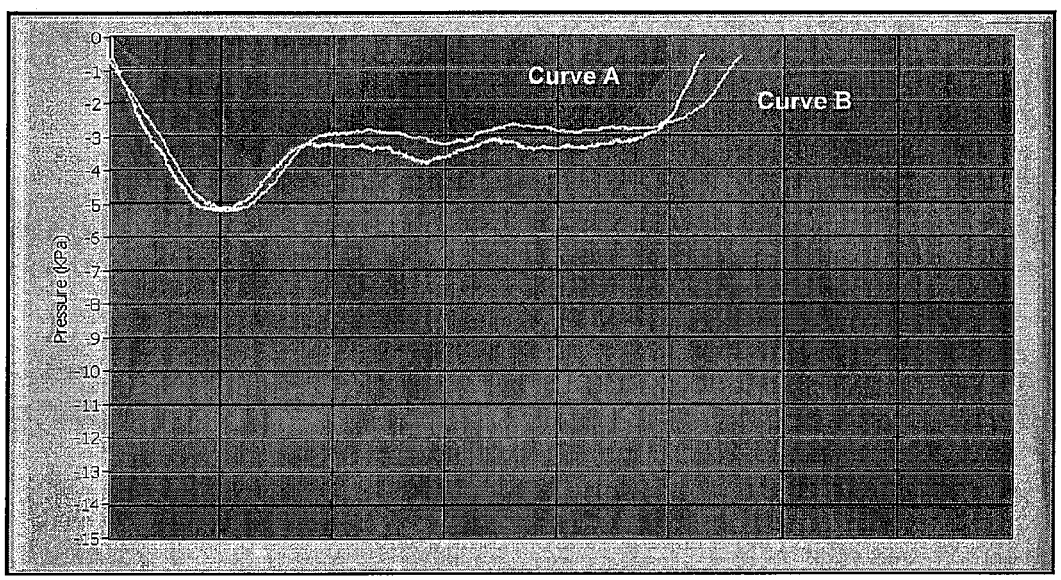
FIG. 22 graphically illustrates an inhalation maneuver performed by a subject (A) using a dry powder inhaler adapted with a sensing and monitoring device as described herein, the graph also illustrates the subject's maneuver recreated by the inhalation stimulation device (B) in real-time.

To assess inhaler performance and determine proper dosing for the patient, the patient is asked to inhale optimally as done previously. As the patient inhales, signals from the training device sensor are transmitted to a receiver of the simulation system in the computer. Upon receiving the signals from the inhaler and data generated from the signal are processed, the simulation inhalation program of the system sends a set of signals to instructs the motor controller of the simulation system to activate the motor and thereby the syringe pump to recreate the patient's inhalation profile which is generated by a pressure differential created in the syringe system and an airflow through the inhaler is created which discharges the powder formulation from a cartridge in the inhaler. The powder plume produced by the inhaler is collected in a filter system connected to the artificial airway, photographed and evaluated for percent dose emitted from the inhaler and the distribution of the particle sizes in the emitted dose. Powder deposition patterns are evaluated inside the artificial model of the upper respiratory tract. After determining the efficiency of dose delivered by the inhaler, the patient dosing requirements are determined for the appropriate amount of powder formulation that the patient will receive as recommended by the physician. FIG. 22 illustrates data obtained from a sensing and monitoring device without a drug as used by the patient and coupled to an inhalation simulation system in real time. As seen in FIG. 22, the patient's inhalation maneuver (curve A) is displayed by the monitor, as well as the inhalation simulation (B) recreated and displayed by the simulation system in real time. The data in FIG. 22 show that the recreated inhalation maneuver is almost identical to the simulation performed by the subject.

The present simulation system allows for an improved system to determine inhaler performance and actual dosing characteristics, attributes and properties resulting from an actual patient inhalation(s) (or those of multiple patients) without exposure to drug. The use of the system also allows for the optimization of inhaler design to meet the requirements of a patient population.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or and consisting essentially of language. When used in the claims, whether as filed or added per amendment, the transition term "consisting of"

excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the abovedescribed elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An inhalation simulation system comprising:
   an artificial anatomical head comprising a substantially accurate upper respiratory airway;
   a dry powder inhaler, wherein the dry powder inhaler is breath-powered;
   a sensor configured within said dry powder inhaler or configured to attach to said dry powder inhaler; said sensor is configured to detect an acoustic signal generated from said dry powder inhaler when said dry powder inhaler is connected to said artificial head and to transmit at least one type of signal to at least one device for analysis, storage, printing or display;
   a vacuum source;
   a power supply;
   a computer comprising a microprocessor, an algorithm and a display device.

2. The inhalation simulation system of claim 1, wherein said dry powder inhaler comprises a sensor and a microprocessor built within the inhaler or provided in a device attachable to the inhaler.

3. The inhalation simulation system of claim 2, wherein said dry powder inhaler device comprises a cartridge comprising a dry powder for pulmonary delivery.

4. The inhalation simulation system of claim 3, wherein the dry powder comprises diketopiperazine microparticles.

5. The inhalation simulation system of claim 3, wherein the dry powder comprises at least one active ingredient.

6. The inhalation simulation system of claim 5, wherein said at least one active ingredient comprises insulin, GLP-1, growth hormone, sumatriptan, parathyroid hormone, or analogs thereof.

7. The inhalation simulation system of claim 2, wherein said dry powder inhaler has a resistance value between about 0.065 ($\sqrt{kPa}$)/liter per minute and about 0.200 ($\sqrt{kPa}$)/liter per minute.

8. The inhalation simulation system of claim 2, wherein an analog to digital converter communicates at least one acoustic signal to a microprocessor configured to analyze and process said at least one acoustic signal.

9. The inhalation simulation system of claim 1, wherein said at least one type of signal is an amplitude of the acoustic signal, a frequency of the acoustic signal or combinations thereof.

10. The inhalation simulation system of claim 1, wherein said sensor is configured to further measure said at least one acoustic signal generated from the inhaler and transmit said signal to a receiver in a microprocessor or a computer.

11. The inhalation simulation system of claim 1, wherein said sensor is a microphone.

12. The inhalation simulation system of claim 1, wherein said sensor is configured to transmit said acoustic signal by a wireless communication mode to said at least one device.

13. The inhalation simulation system of claim 1, wherein said at least one device is an analog to digital converter.

14. The inhalation simulation system of claim 1, wherein said at least one device is a display device.

15. The inhalation simulation system of claim 14, wherein the display device is a computer monitor, a PDA or a printer.

16. The inhalation simulation system of claim 1, wherein the vacuum source is a calibrated syringe pump or a piston/cylinder device.

17. A method for simulating an inhalation maneuver by a subject, comprising:
   providing a first breath-powered dry powder inhaler comprising a first sensor and a first radio transmitter to the subject, wherein the first sensor is configured within said breath-powered dry powder inhaler or attached to said breath-powered dry powder inhaler;
   having the subject inhale through the first breath-powered dry powder inhaler to produce a pressure differential through the first breath-powered dry powder inhaler in a location near an inhalation simulation apparatus, inhalation simulation apparatus comprising:
      a computer with a microprocessor comprising a signal receiver and an algorithm configured to analyze and process a signal produced from the first sensor,
      a controller,
      a motor,
      a calibrated syringe pump,
      an artificial substantially accurate anatomical upper respiratory airway, and
      a second breath-powered dry powder inhaler attached to said artificial substantially accurate anatomical upper respiratory airway and comprising a second sensor, a second radio transmitter and a dry powder formulation;

collecting at least one type of signal from flow generated in the first breath-powered dry powder inhaler;

converting the signal to a first set of data from the subject's inhalation provided by the first sensor in the computer or microprocessor with said algorithm;

generating a second set of signals in the computer to instruct the controller to activate the motor to move the calibrated syringe pump to generate a pressure differential equal to the pressure differential generated by the subject's inhalation; and simulating said inhalation maneuver by said subject.

18. The method of claim 17, wherein the syringe pump is connected to the artificial substantially accurate anatomical upper respiratory airway configured with a mouth connected to the second inhaler.

19. The method of claim 17, wherein the second inhaler is a dry powder inhaler adapted with a sensor and a radio transmitter.

20. The method of claim 17, wherein the second inhaler is adapted with a wireless or wired jacket comprising a microphone which can convert a sound signal into an electrical impulse configured to communicate with a radio signal receiver in a computer or microprocessor.

* * * * *